US012390461B2

(12) United States Patent
Fouda et al.

(10) Patent No.: US 12,390,461 B2
(45) Date of Patent: Aug. 19, 2025

(54) MODULATORS OF RAR-RELATED ORPHAN RECEPTORS (RORs)

(71) Applicant: 11949098 CANADA INC., Brossard (CA)

(72) Inventors: Ahmed Fouda, Montreal (CA); Jean Tchervenkov, Brossard (CA); Steven Paraskevas, Montreal (CA); Sarita Negi, Montreal (CA)

(73) Assignee: 11949098 CANADA INC., Brossard (CA)

(*) Notice: Subject to any disclaimer, the term of this patent is extended or adjusted under 35 U.S.C. 154(b) by 30 days.

(21) Appl. No.: 17/294,915

(22) PCT Filed: Nov. 19, 2019

(86) PCT No.: PCT/CA2019/051644

§ 371 (c)(1),
(2) Date: May 18, 2021

(87) PCT Pub. No.: WO2020/102889

PCT Pub. Date: May 28, 2020

(65) Prior Publication Data

US 2022/0000864 A1 Jan. 6, 2022

Related U.S. Application Data

(60) Provisional application No. 62/769,849, filed on Nov. 20, 2018, provisional application No. 62/769,167, filed on Nov. 19, 2018.

(51) Int. Cl.
*C07D 409/14* (2006.01)
*A61K 31/047* (2006.01)
(Continued)

(52) U.S. Cl.
CPC .......... *A61K 31/498* (2013.01); *A61K 31/047* (2013.01); *A61K 31/131* (2013.01);
(Continued)

(58) Field of Classification Search
None
See application file for complete search history.

(56) References Cited

U.S. PATENT DOCUMENTS

2009/0163545 A1 6/2009 Goldfarb

FOREIGN PATENT DOCUMENTS

WO WO-2011136269 A1 * 11/2011 .......... A61K 31/381
WO WO-2013142628 A2 * 9/2013 .......... A61K 31/495

OTHER PUBLICATIONS

Reddy and al., Anti-Inflammatory& Antioxidant of Some New Acid Chloridederivatives of 2-Amino-N-(3-Chlorophenyl)-4, 5, 6, 7-Tetrahydrobenzo[b] Thiophene-3-Carboxamide, Pharmacologyonline 2: 572-574 (2009).

(Continued)

*Primary Examiner* — Jeffrey S Lundgren
*Assistant Examiner* — Anthony Joseph Seitz
(74) *Attorney, Agent, or Firm* — BENOIT & CÔTÉ

(57) ABSTRACT

The invention encompasses the novel class of compounds represented by the Formula (I), (II), (III) and (IV) below, which are modulators of RORγt:

(Continued)

(I)

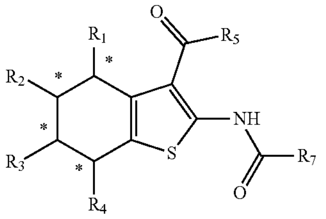

(II)

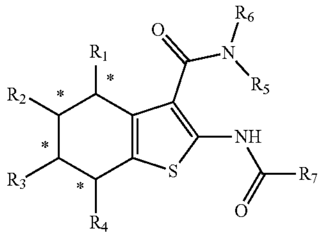

(III)

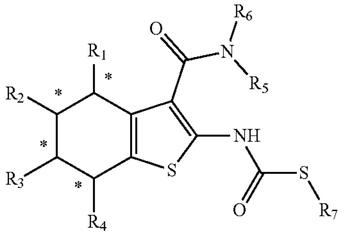

(IV)

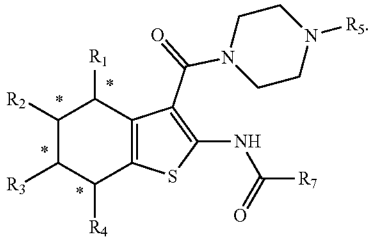

The invention also encompasses pharmaceutical compositions which include the compounds shown above and methods of treating or preventing autoimmune diseases and antibody mediated rejection in a patient in need thereof.

14 Claims, 6 Drawing Sheets

(51) Int. Cl.

| | |
|---|---|
| ***A61K 31/131*** | (2006.01) |
| ***A61K 31/17*** | (2006.01) |
| ***A61K 31/196*** | (2006.01) |
| ***A61K 31/198*** | (2006.01) |
| ***A61K 31/255*** | (2006.01) |
| ***A61K 31/381*** | (2006.01) |
| ***A61K 31/404*** | (2006.01) |
| ***A61K 31/407*** | (2006.01) |
| ***A61K 31/4155*** | (2006.01) |
| ***A61K 31/4178*** | (2006.01) |
| ***A61K 31/436*** | (2006.01) |
| ***A61K 31/44*** | (2006.01) |
| ***A61K 31/465*** | (2006.01) |
| ***A61K 31/475*** | (2006.01) |
| ***A61K 31/496*** | (2006.01) |
| ***A61K 31/497*** | (2006.01) |
| ***A61K 31/498*** | (2006.01) |
| ***A61K 31/506*** | (2006.01) |
| ***A61K 31/513*** | (2006.01) |
| ***A61K 31/519*** | (2006.01) |
| ***A61K 31/52*** | (2006.01) |
| ***A61K 31/5517*** | (2006.01) |
| ***A61K 31/655*** | (2006.01) |
| ***A61K 31/675*** | (2006.01) |
| ***A61K 31/7008*** | (2006.01) |
| ***A61K 31/704*** | (2006.01) |
| ***A61K 31/7068*** | (2006.01) |
| ***A61K 33/243*** | (2019.01) |
| ***A61K 35/17*** | (2025.01) |
| ***A61K 38/12*** | (2006.01) |
| ***A61K 38/14*** | (2006.01) |
| ***A61K 38/19*** | (2006.01) |
| ***A61K 39/395*** | (2006.01) |
| ***A61K 45/06*** | (2006.01) |
| ***A61P 37/06*** | (2006.01) |
| ***C07D 333/66*** | (2006.01) |
| ***C07D 409/04*** | (2006.01) |
| ***C07D 409/06*** | (2006.01) |
| ***C07D 409/12*** | (2006.01) |

(52) U.S. Cl.

CPC ............ *A61K 31/17* (2013.01); *A61K 31/196* (2013.01); *A61K 31/198* (2013.01); *A61K 31/255* (2013.01); *A61K 31/381* (2013.01); *A61K 31/404* (2013.01); *A61K 31/407* (2013.01); *A61K 31/4155* (2013.01); *A61K 31/4178* (2013.01); *A61K 31/436* (2013.01); *A61K 31/44* (2013.01); *A61K 31/465* (2013.01); *A61K 31/475* (2013.01); *A61K 31/496* (2013.01); *A61K 31/497* (2013.01); *A61K 31/506* (2013.01); *A61K 31/513* (2013.01); *A61K 31/519* (2013.01); *A61K 31/52* (2013.01); *A61K 31/5517* (2013.01); *A61K 31/655* (2013.01); *A61K 31/675* (2013.01); *A61K 31/7008* (2013.01); *A61K 31/704* (2013.01); *A61K 31/7068* (2013.01); *A61K 33/243* (2019.01); *A61K 35/17* (2013.01); *A61K 38/12* (2013.01); *A61K 38/14* (2013.01); *A61K 38/191* (2013.01); *A61K 39/3955* (2013.01); *A61K 45/06* (2013.01); *A61P 37/06* (2018.01); *C07D 333/66* (2013.01); *C07D 409/04* (2013.01); *C07D 409/06* (2013.01); *C07D 409/12* (2013.01); *C07D 409/14* (2013.01)

(56) References Cited

OTHER PUBLICATIONS

Manpreet and al., Crystal structure of N-(3-benzoyl-4,5,6,7-tetrahydro-1-benzothiophen-2-yl)benzamide, Acta Cryst. (2014). E70, o951-o952.

Kharizomenova and al., Functional Derivatives of Thiophene. XXI.* Synthesis and Antiviral Activity, of 2-Benzoy LAMI1NO-3-o~-Hydi~Oxyalky L-4,5-Dialky Lthiophenes, S. Ordzhonikidze All-Union Pharmaceutical ChemistryResearch Institute, Moscow. Translated from Khimiko-farmatsevticheskii Zhurnal, vol. 19, No. 9, pp. 1079-1080, Sep. 1985. Original article submitted Oct. 1, 1984. 0091-.

Cao and al., Discovery of Novel Tubulin Inhibitors via Structure-Based Hierarchical Virtual Screening, Journal of Chemical Information and Modeling (2012), vol. 52, 2730-2740.

(56) References Cited

OTHER PUBLICATIONS

Stroganova and al., Opening of the Furan Ring in 2-R-Amino-3-Furfurylthiophenes By the Action of Acids, Chemistry of Heterocyclic Compounds, vol. 47, No. 1, Apr. 2011, Russian Original vol. 47, No. 1, Jan. 2011.
Massari and al., Structural Investigation of Cycloheptathiophene-3-carboxamide Derivatives Targeting Influenza Virus Polymerase Assembly, Journal of Medicinal Chemistry (2013), vol. 56, 10118-10131.
Mahmoud and al., Synthesis and antitumor evaluation of noveltet rahydrobenzo[4',5']thieno[3',2':5,6]pyrimido[1,2-b]isoquinoline derivatives, Synthetic Communications® (2018), vol. 48, No. 4, 428-438, https://doi.org/10.1080/00397911.2017.1406520.
Abdalha and al., Synthesis of Some New Tetrahydrobenzo[b]thiophene Derivatives and Tetrahydrobenzothienopyrimidine DerivativesUnder Microwave Irradiation, Synthetic Communications1, 41: 2811-2821, 2011 Copyright # Taylor & Francis Group, LLC, ISSN: 0039-7911 print=1532-2432 online, DOI: 10.1080/00397911.2010.501479.
SciFinder® D10-15, D17-21 and D24, American Chemical Society (ACS).

* cited by examiner (I)

(II)

(III)

(IV)

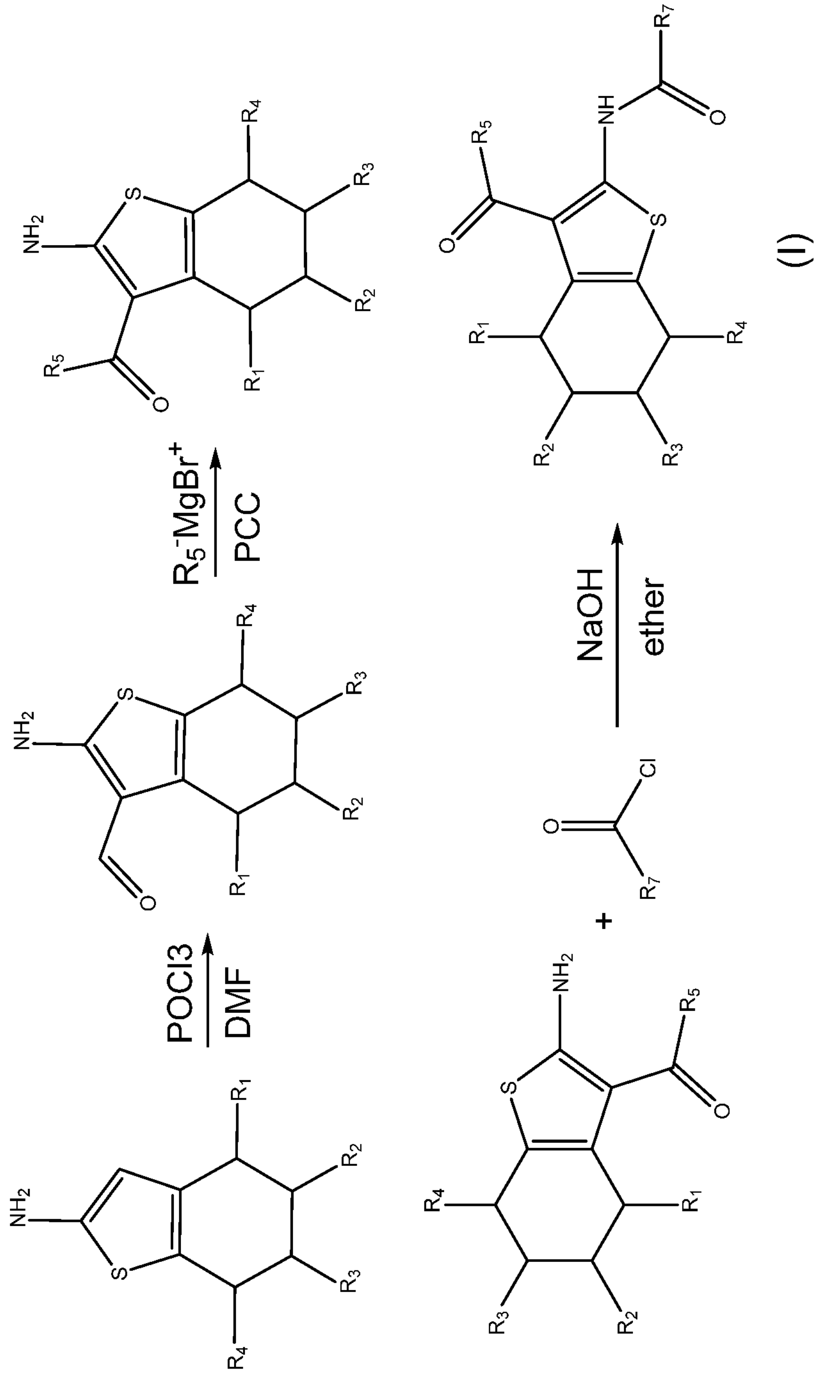
3A
3B
(I)
FIG. 3A-B

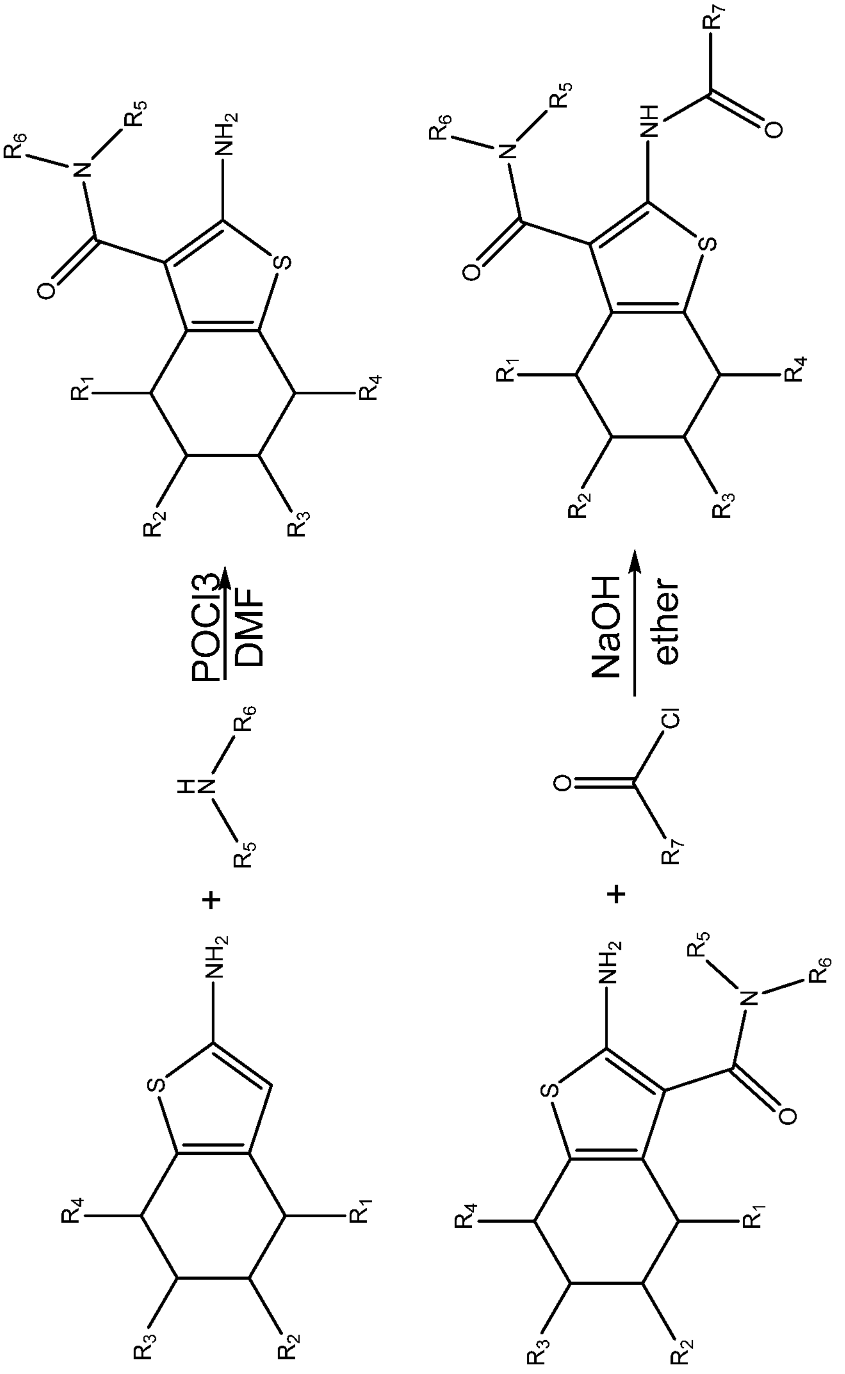
4A
4B
(II)
FIG. 4A-B

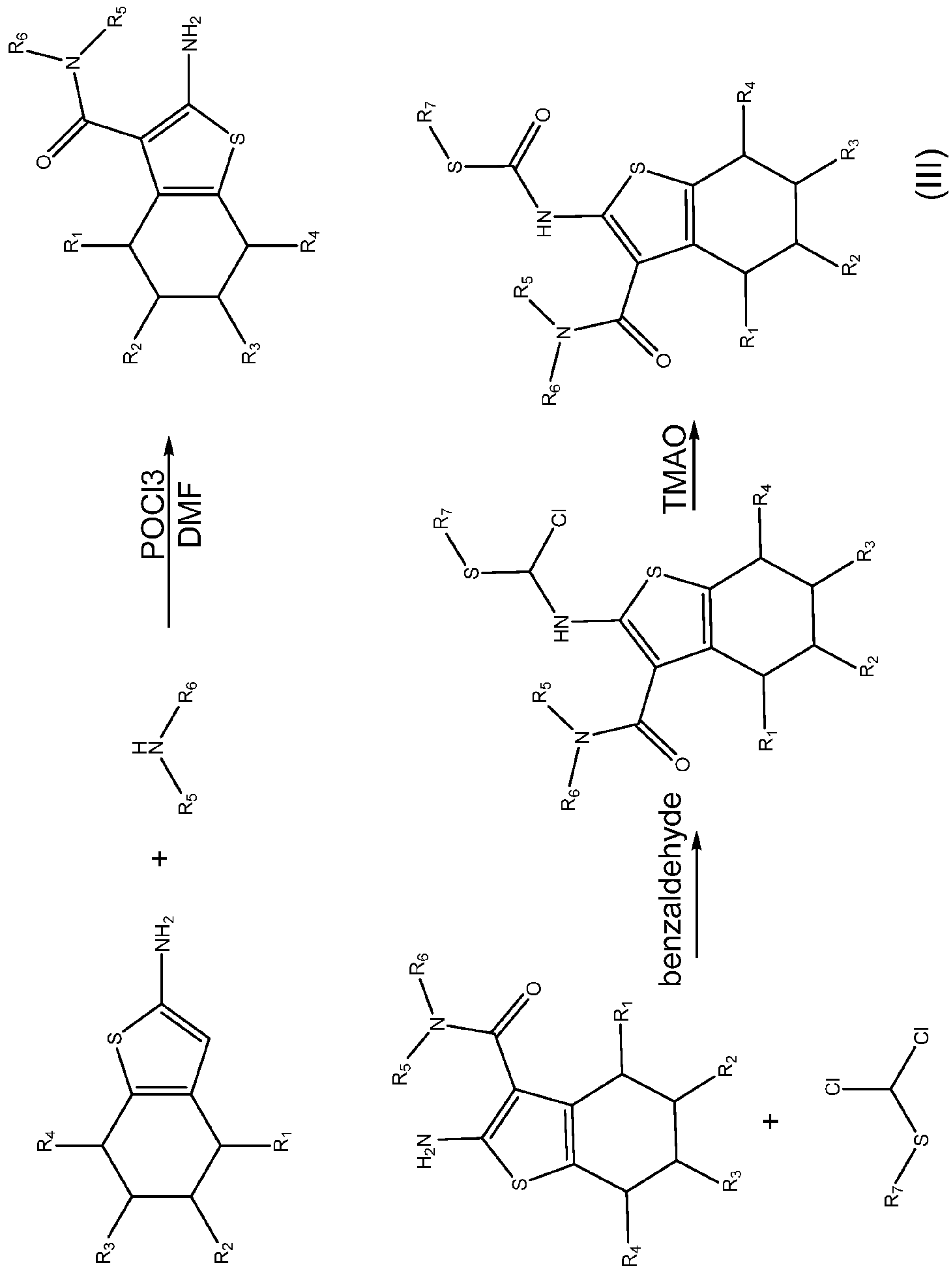
(III)
5A
5B
FIG. 5A-B

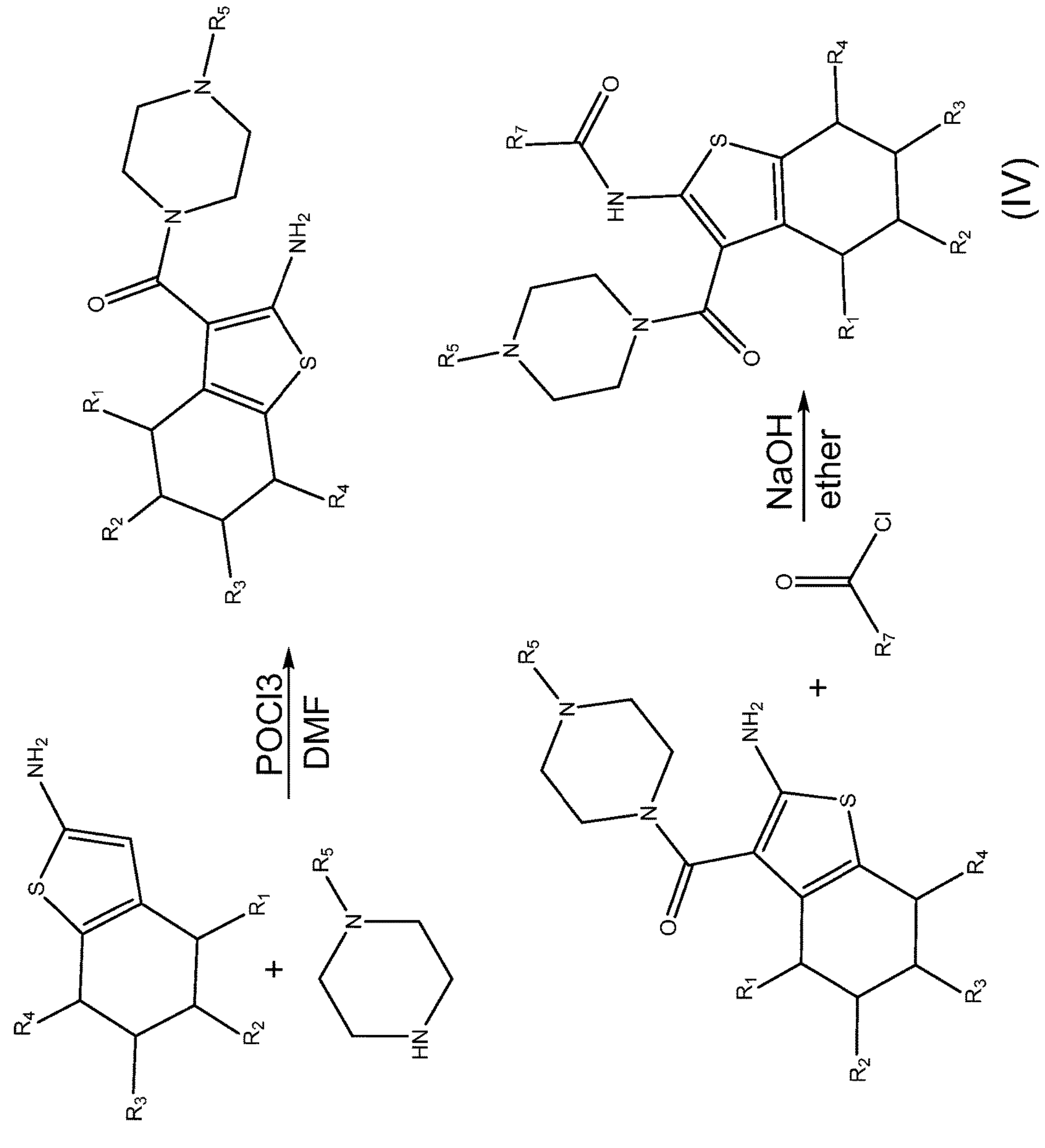
6A
6B
(IV)
FIG. 6A-B

MODULATORS OF RAR-RELATED ORPHAN RECEPTORS (RORs)

FIELD OF THE INVENTION

This invention relates to novel modulators of retinoic-acid-receptor-related (RAR) orphan nuclear receptors (RORs) alpha (RORα or RORA) and gamma (RORC, RORγ or RORγt) and their use in the control of autoimmune diseases, antibody mediated allograft rejection, and other associated diseases involving increased or decreased activity of RORα or RORγt or their controlled genes and gene products which include many types of cancers, metabolic and inflammatory disorders.

BACKGROUND

An autoimmune disease is a condition arising from an abnormal immune response to a normal body part. There are at least many types of autoimmune diseases. Nearly any body part can be involved. Common symptoms include low grade fever and feeling tired. Often symptoms come and go.

The cause is generally unknown. Some autoimmune diseases such as lupus run in families, and certain cases may be triggered by infections or other environmental factors. Some common diseases that are generally considered autoimmune include celiac disease, diabetes mellitus type 1, Graves' disease, inflammatory bowel disease, multiple sclerosis, psoriasis, rheumatoid arthritis, and systemic lupus erythematosus. The diagnosis can be difficult to determine.

Treatment depends on the type and severity of the condition. Nonsteroidal anti-inflammatory drugs (NSAIDs) and immunosuppressants are often used. Intravenous immunoglobulin may also occasionally be used. While treatment usually improves symptoms, they do not typically cure the disease.

Chronic antibody injury is a serious threat to allograft outcomes and is therefore the center of active research. In the continuum of allograft rejection, the development of antibodies plays a critical role. In recent years, an increased recognition of molecular and histologic changes has provided a better understanding of antibody-mediated rejection (AMR), as well as potential therapeutic interventions. However, several pathways are still unknown, which accounts for the lack of efficacy of some of the currently available agents that are used to treat rejection.

The retinoic acid receptor-related (ROR) sub-family of orphan nuclear receptors was initially identified on the basis of sequence similarities to the retinoic acid and retinoid X receptor families. Through alternative promoter usage and exon splicing, the ROR genes encode different isoforms of RORα, β and γ, which exhibit differential tissue expression and functions. RORγt is a differentially spliced isoform of RORγ, that differs only in the N-terminus by the presence of 21 additional amino acids in RORγ. The endogenous physiological ligands for RORγt have recently been identified as 7β-27-dihydroxy cholesterol, and two other cholesterol biosynthetic intermediates.

RORγt is exclusively expressed in cells of the immune system including $CD4^+$ $CD8^+$ double positive thymocytes 5, Th17, Tc17, and γδ T cells, as well as a subset of innate lymphoid cells (ILCs) and regulatory T cells (Tregs). RORγt is a key transcription factor driving Th17 cell differentiation, and production of IL-17A, IL-17F and IL-22 in innate and adaptive immune cells, also termed "type 17" cells. Th17 cytokines, IL-17A, IL-17F, and IL-22, stimulate tissue cells to produce a panel of inflammatory chemokines, cytokines and metalloproteases, resulting in the recruitment of granulocytes to sites of inflammation. The Th17 cell subset has been shown to be the major pathogenic population in several models of autoimmune inflammation, including collagen-induced arthritis (CIA) and experimental autoimmune encephalomyelitis (EAE). RORγt deficient mice show impaired Th17 cell differentiation in vitro, significantly reduced Th17 cell populations in vivo, and decreased susceptibility to EAE and intestinal inflammation. RORγt-deficient T cells fail to induce colitis in the mouse T cell transfer model.

Human genetic studies have shown association of polymorphisms in the genes for Th17 cell-surface receptors, IL-23R and CCR6, with susceptibility to inflammatory bowel disease (IBD), multiple sclerosis (MS), rheumatoid arthritis (RA) ankylosing spondylitis (AS) and psoriasis. Clinical modulation of the IL-23/IL-17 pathway through biologics targeting IL-12/23, IL-23, IL-17A or IL-17RA has provided validation of its critical role in human autoimmune diseases. RORγt is a nuclear receptor target in the IL-23/IL-17 pathway and has been shown to be tractable to modulation by oral small molecules. Indeed, other nuclear receptors have been successfully targeted by orally available small molecules that are now marketed drugs.

There is a need to have modulators that inhibit the activity of RORs to control autoimmune diseases and antibody mediated rejection. Other modulators can activate RORs and can be useful in the treatment of many types of lymphomas and cancer. A modulator effect is a pharmacological effect that can be stimulatory or inhibitory. The modulators can be categorized as activators or inhibitors. They can be also categorized as agonists, antagonists, partial agonists and inverse agonists.

SUMMARY

According to an aspect, there is provided a compound of Formula (I), (II) (III), or (IV) a pharmaceutically acceptable salts thereof, or stereoisomers thereof:

(I)

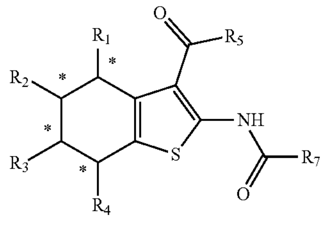

(II)

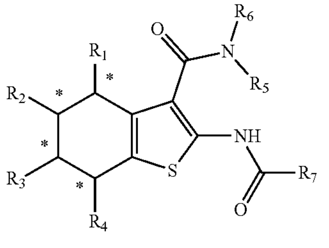

-continued (III)

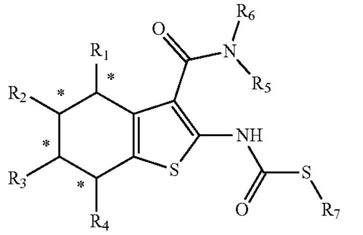

(IV)

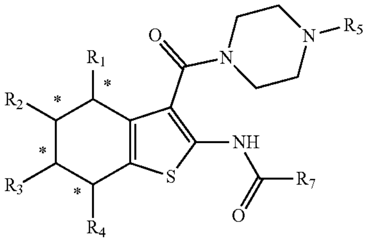

wherein, $R_1$, $R_2$, $R_3$, and/or $R_4$ group(s) is/are H, halogen, $NO_2$, 1-6 alkoxy, OH, $NH_2$, 1-6 alkyl, 1-6 alkenyl, 1-6 haloalkyl, N-dialkyl, haloalkoxy, 1-6 hydroxyalkyl, and/or —$CO_2$ (1-6 alkyl), $R_5$ is a substituted or unsubstituted five or six membered saturated or unsaturated heterocycle, aryl, (alkylarene), halo aryl, ring substituted arylalkyl, ring substituted alkyl-hexane, ring substituted alkyl-cyclopentane, haloaryl, benzene, phenyl, pyridine, pyrimidine, pyridine, imidazole, diazole, triazole, thiadiazole, imidazolidine, thizolidine, pyrrolidine, piperazine, piperidine, pyridazine, pyrazine, triazine, 1H pyrrole, 2H pyrrole, pyrroline, pyrazolidine, pyrazoline, thiazole, isothiazole, isoxazole, haloalkyl, orcyanoalkyl, methylpyrimidine, toluene, methylpyridine, methylimidazole, methyldiazole, methyltriazole, methylthiadiazole, methylimidazolidine, methylthizolidine, methylpyrrolidine, methylpiperazine, methylpiperidine, methylpyridazine, methylpyrazine, methyltriazine, methylpyrrole, methylpyrroline, methylpyrazolidine, methylpyrazoline, methylthiazole, methylisothiazole, methylisoxazole, or arylalkyl.

$R_6$ is H, 1-6 alkyl, or may form a five or six ring structure with $R_5$; and $R_7$ is a substituted or unsubstituted five or six membered saturated or unsaturated heterocycle, ring substituted alkylarene, ring substituted alkyl-hexane, ring substituted alkyl-cyclopentane, substituted haloaryl, substituted benzene, substituted phenyl, benzyl, pyrimidine, pyridine, imidazole, diazole, triazole, thiadiazole, imidazolidine, thizolidine, pyrrolidine, piperazine, aryl, halo aryl, alkylarene, piperidine, pyridazine, pyrazine, triazine, 1H pyrrole, 2H pyrrole, pyrroline, pyrazolidine, pyrazoline, thiazole, isothiazole, isoxazole, cyanolkyl, methylpyrimidine, toluene, methylpyridine, methylimidazole, methyldiazole, methyltriazole, methylthiadiazole, methylimidazolidine, methylthizolidine, methylpyrrolidine, methylpiperazine, methylpiperidine, methylpyridazine, methylpyrazine, methyltriazine, methylpyrrole, methylpyrroline, methylpyrazolidine, methylpyrazoline, methylthiazole, methylisothiazole, methylisoxazole, or arylalkyl.

In an embodiment, the compounds of Formula (I), (II), (III), or (IV) pharmaceutically acceptable salts thereof, or stereoisomers thereof is selected from the group consisting of:

N-(3-(4-benzylpiperazine-1-carbonyl)-4,5,6,7-tetrahydrobenzo[b]thiophen-2-yl)-2-fluorobenzamide;

N-(3-(benzylcarbamoyl)-4,5,6,7-tetrahydrobenzo[b]thiophen-2-yl)-5-chloro-2-(methylthio)pyrimidine-4-carboxamide;

5-chloro-N-(3-{[(1,1-dioxidotetrahydro-3-thienyl)amino]-carbonyl}-6-methyl-4,5,6,7-tetrahydro-1-benzothien-2-yl)-2-(methylthio)-4-pyrimidine-carboxamide;

N-(6-ethyl-3-{[(2-methylphenyl)amino]carbonyl}-4,5,6,7-tetrahydro-1-benzothien-2-yl)-1-methyl-1H-pyrazole-5-carboxamide;

N-{6-tert-butyl-3-[(4-methyl-1-piperazinyl)carbonyl]-4,5,6,7-tetrahydro-1-benzothien-2-yl}-2-fluorobenzamide;

2-fluoro-N-{6-methyl-3-[(4-methyl-1-piperazinyl)carbonyl]-4,5,6,7-tetrahydro-1-benzothien-2-yl}benzamide;

N-benzyl-2-[(trifluoroacetyl)amino]-4,5,6,7-tetrahydro-1-benzothiophene-3-carboxamide;

N-benzyl-2-({[(4-methyl-2-pyrimidinyl)thio] acetyl}amino)-4,5,6,7-tetrahydro-1-benzothiophene-3-carboxamide;

N-benzyl-2-[(1-piperidinylacetyl)amino]-4,5,6,7-tetrahydro-1-benzothiophene-3-carboxamide;

N-benzyl-2-{[(4-methyl-1-piperazinyl)acetyl]amino}-4,5,6,7-tetrahydro-1-benzothiophene-3-carboxamide;

N-benzyl-2-{[(4-methyl-1-piperidinyl)acetyl]amino}-4,5,6,7-tetrahydro-1-benzothiophene-3-carboxamide;

N-(3-(2-methylpyrrolidine-1-carbonyl)-4,5,6,7-tetrahydrobenzo[b]thiophen-2-yl)nicotinamide;

N-(3-((2R,4R)-2,4-dimethylpiperidine-1-carbonyl)-4,5,6,7-tetrahydrobenzo[b]thiophen-2-yl)nicotinamide;

N-(3-(((1r,4r)-4-hydroxycyclohexyl)carbamoyl)-4,5,6,7-tetrahydrobenzo[b]thiophen-2-yl)nicotinamide;

N-(3-(3-ethylpyrrolidine-1-carbonyl)-4,5,6,7-tetrahydrobenzo[b]thiophen-2-yl)nicotinamide;

N-benzyl-2-(2-((1-methyl-1H-imidazol-2-yl)thio)acetamido)-4,5,6,7-tetrahydrobenzo[b]thiophene-3-carboxamide;

N-(3-(3-(hydroxymethyl)pyrrolidine-1-carbonyl)-4,5,6,7-tetrahydrobenzo[b]thiophen-2-yl)nicotinamide;

N-(6,6-dimethyl-3-(morpholine-4-carbonyl)-4,5,6,7-tetrahydrobenzo[b]thiophen-2-yl)pyrazine-2-carboxamide;

N-(3-(((1-methyl-1H-1,2,4-triazol-3-yl)methyl)carbamoyl)-4,5,6,7-tetrahydrobenzo[b]thiophen-2-yl)nicotinamide;

(S)—N-(3-((1-cyanoethyl)carbamoyl)-4,5,6,7-tetrahydrobenzo[b]thiophen-2-yl)nicotinamide;

N-(3-((piperidin-4-ylmethyl)carbamoyl)-4,5,6,7-tetrahydrobenzo[b]thiophen-2-yl)nicotinamide;

N-(3-benzoyl-4,5,6,7-tetrahydrobenzo[b]thiophen-2-yl) pyrazine-2-carboxamide; and N-(3-benzoyl-4,5,6,7-tetrahydrobenzo[b]thiophen-2-yl)-5-methyl-2-(methylsulfonyl)pyrimidine-4-carboxamide.

According to an aspect, there is provided a pharmaceutical composition comprising at least one compound of Formula (I), (II), III), or (IV) a pharmaceutically acceptable salt thereof, or a stereoisomer thereof, and a pharmaceutically acceptable carrier.

According to an aspect, there is provided a use of the compound of Formula (I), (II), (III), or (IV) pharmaceutically acceptable salts thereof, or stereoisomers thereof in the manufacture of a medicament for modulating RORs and/or controlling autoimmune diseases and antibody mediated rejection in a patient.

According to an aspect, there is provided a use of a therapeutically effective amount of any one of the compounds of Formula (I), (II), (III), or (IV) pharmaceutically acceptable salts thereof, or stereoisomers thereof for preventing or treating a RORs mediated disease or autoimmune disease in a patient in need of treatment or antibody mediated rejection in a patient.

In an embodiment, said RORs mediated disease or autoimmune disease is cancer, celiac disease, diabetes mellitus type 1, Graves' disease, inflammatory bowel disease, multiple sclerosis, psoriasis, rheumatoid arthritis, systemic lupus erythematosus, asthma, dermatitis, fatty liver disease, Crohn's disease, cardiovascular disease, inflammatory diseases, neurological disorder, multiple sclerosis and arteriosclerosis.

In an embodiment, said cancer is prostate cancer, breast cancer, ovarian cancer, multiple myeloma, brain cancer, glioma, lung cancer, salivary cancer, stomach cancer, thymic epithelial cancer, thyroid cancer, leukemia, melanoma, lymphoma, gastric cancer, pancreatic cancer, kidney cancer, bladder cancer, colon cancer and liver cancer.

According to an aspect, there is provided a pharmaceutical composition comprising:

(1) a first compound of Formula (I), (II), (III), or (IV) pharmaceutically acceptable salt thereof, or stereoisomer thereof according to any one of claims 1 to 2;

(2) one or more additional compounds selected from the group consisting of:

(a) a cytotoxic agent;
(b) an antimetabolite;
(c) an alkylating agent;
(d) an anthracycline;
(e) an antibiotic;
(f) an anti-mitotic agent;
(g) a hormone therapy;
(h) a signal transduction inhibitor;
(i) a gene expression modulator;
(j) an apoptosis inducer;
(k) an angiogenesis inhibitor;
(l) an immunotherapy agent;
and (3) a pharmaceutically acceptable carrier.

In an embodiment, said cytotoxic agent is taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, analogs or homologs thereof, or a combination thereof.

In an embodiment, said antimetabolite is methotrexate, 6-mercaptopurine, 6-thioguanine, cytarabine, 5-fluorouracil decarbazine, or a combination thereof.

In an embodiment, said alkylating agent is mechlorethamine, thioepa chlorambucil, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, or a combination thereof.

In an embodiment, said anthracycline is daunorubicin, doxorubicin, or a combination thereof.

In an embodiment, said antibiotic is dactinomycin, bleomycin, mithramycin, anthramycin (AMC), or a combination thereof.

In an embodiment, said anti-mitotic agent is vincristine, vinblastine, or a combination thereof.

In an embodiment, said signal transduction inhibitor is imatinib, trastuzumab, or a combination thereof.

In an embodiment, said gene expression modulator is a siRNA, a shRNA, an antisense oligonucleotide, an HDAC inhibitor, or a combination thereof.

In an embodiment, said immunotherapy agent is a monoclonal antibody, a chimeric antigen receptors (CARs) T-Cell, or a combination thereof.

In an embodiment, said hormone therapy is a luteinizing hormone-releasing hormone (LHRH) antagonist.

In an embodiment, said apoptosis inducer is a recombinant human TNF-related apoptosis-inducing ligand (TRAIL).

In an embodiment, said angiogenesis inhibitor is sorafenib, sunitinib, pazopanib, everolimus or a combination thereof.

In an embodiment, said first compound is selected from the group consisting of:

N-(3-(4-benzylpiperazine-1-carbonyl)-4,5,6,7-tetrahydrobenzo[b]thiophen-2-yl)-2-fluorobenzamide;
N-(3-(benzylcarbamoyl)-4,5,6,7-tetrahydrobenzo[b]thiophen-2-yl)-5-chloro-2-(methylthio)pyrimidine-4-carboxamide;
5-chloro-N-(3-{[(1,1-dioxidotetrahydro-3-thienyl)amino]-carbonyl}-6-methyl-4,5,6,7-tetrahydro-1-benzothien-2-yl)-2-(methylthio)-4-pyrimidine-carboxamide;
N-(6-ethyl-3-{[(2-methylphenyl)amino]carbonyl}-4,5,6,7-tetrahydro-1-benzothien-2-yl)-1-methyl-1H-pyrazole-5-carboxamide;
N-{6-tert-butyl-3-[(4-methyl-1-piperazinyl)carbonyl]-4,5,6,7-tetrahydro-1-benzothien-2-yl}-2-fluorobenzamide;
2-fluoro-N-{6-methyl-3-[(4-methyl-1-piperazinyl)carbonyl]-4,5,6,7-tetrahydro-1-benzothien-2-yl}benzamide;
N-benzyl-2-[(trifluoroacetyl)amino]-4,5,6,7-tetrahydro-1-benzothiophene-3-carboxamide;
N-benzyl-2-({[(4-methyl-2-pyrimidinyl)thio]acetyl}amino)-4,5,6,7-tetrahydro-1-benzothiophene-3-carboxamide;
N-benzyl-2-[(1-piperidinylacetyl)amino]-4,5,6,7-tetrahydro-1-benzothiophene-3-carboxamide;
N-benzyl-2-{[(4-methyl-1-piperazinyl)acetyl]amino}-4,5,6,7-tetrahydro-1-benzothiophene-3-carboxamide;
N-benzyl-2-{[(4-methyl-1-piperidinyl)acetyl]amino}-4,5,6,7-tetrahydro-1-benzothiophene-3-carboxamide;
N-(3-(2-methylpyrrolidine-1-carbonyl)-4,5,6,7-tetrahydrobenzo[b]thiophen-2-yl)nicotinamide;
N-(3-((2R,4R)-2,4-dimethylpiperidine-1-carbonyl)-4,5,6,7-tetrahydrobenzo[b]thiophen-2-yl)nicotinamide;
N-(3-(((1r,4r)-4-hydroxycyclohexyl)carbamoyl)-4,5,6,7-tetrahydrobenzo[b]thiophen-2-yl)nicotinamide;
N-(3-(3-ethylpyrrolidine-1-carbonyl)-4,5,6,7-tetrahydrobenzo[b]thiophen-2-yl)nicotinamide;
N-benzyl-2-(2-((1-methyl-1H-imidazol-2-yl)thio)acetamido)-4,5,6,7-tetrahydrobenzo[b]thiophene-3-carboxamide;
N-(3-(3-(hydroxymethyl)pyrrolidine-1-carbonyl)-4,5,6,7-tetrahydrobenzo[b]thiophen-2-yl)nicotinamide;
N-(6,6-dimethyl-3-(morpholine-4-carbonyl)-4,5,6,7-tetrahydrobenzo[b]thiophen-2-yl)pyrazine-2-carboxamide;
N-(3-(((1-methyl-1H-1,2,4-triazol-3-yl)methyl)carbamoyl)-4,5,6,7-tetrahydrobenzo[b]thiophen-2-yl)nicotinamide;
(S)—N-(3-((1-cyanoethyl)carbamoyl)-4,5,6,7-tetrahydrobenzo[b]thiophen-2-yl)nicotinamide;
N-(3-((piperidin-4-ylmethyl)carbamoyl)-4,5,6,7-tetrahydrobenzo[b]thiophen-2-yl)nicotinamide;
N-(3-benzoyl-4,5,6,7-tetrahydrobenzo[b]thiophen-2-yl)pyrazine-2-carboxamide;

N-(3-benzoyl-4,5,6,7-tetrahydrobenzo[b]thiophen-2-yl)-5-methyl-2-(methylsulfonyl)pyrimidine-4-carboxamide; and a combination thereof.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIGS. 3A-B illustrate two step synthesis schemes of compounds represented by the general formula (I) starting with a substituted 2-amino-4,5,6,7-tetrahydro-1-benzothiophene bearing $R_1$-$R_4$ groups, $R_5^-MgBr^+$ and acyl chloride derivatives coupled to a $R_7$ group;

FIGS. 4A-B illustrate two step synthesis scheme of compounds represented by the general formula (II) starting with a substituted 2-amino-4,5,6,7-tetrahydro-1-benzothiophene bearing $R_1$-$R_4$ groups, secondary amine bearing $R_5$ and $R_6$ groups, and acyl chloride coupled to $R_7$ group;

FIGS. 5A-B illustrate two step synthesis scheme of compounds represented by the general formula (III) starting with a substituted 2-amino-4,5,6,7-tetrahydro-1-benzothiophene bearing $R_1$-$R_4$ groups, a secondary amine coupled to $R_5$ and $R_6$ groups, and dichloromethyl sulfide coupled to a $R_7$; and FIGS. 6A-B illustrate two step synthesis scheme of compounds represented by the general formula (IV) starting with a substituted 2-amino-4,5,6,7-tetrahydro-1-benzothiophene bearing $R_1$-$R_4$ groups, a piperazine derivative coupled to a $R_5$ group, and acyl chloride coupled to $R_7$ group.

DETAILED DESCRIPTION

Figure 1:
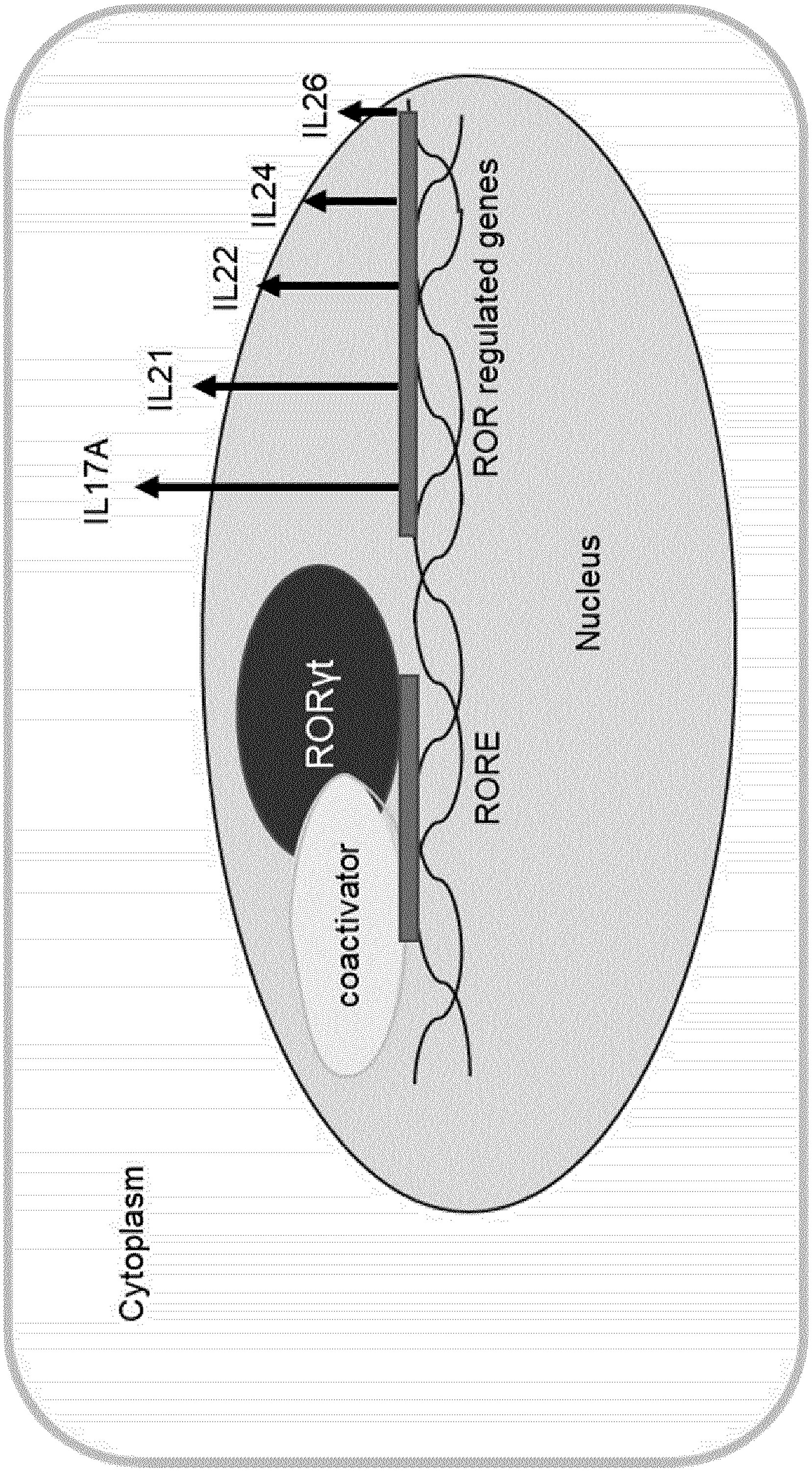
FIG. 1 illustrates RORγt controlled genes in lymphocytes. The illustrations represent a lymphocyte that secrete either one, few or several cytokines regulated by RORγt nuclear receptor. Lymphocytes are named (e.g. Th17, Tc17, TFH, Th17/TFH or Th22) based on the predominant cytokine(s) secreted.
Figure 2:
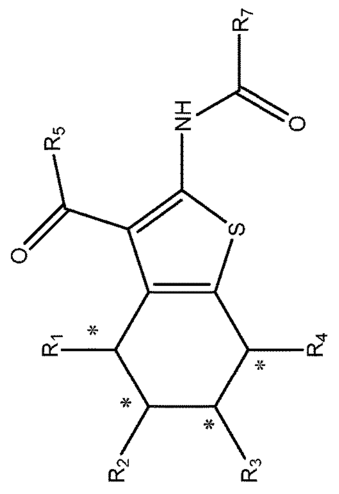
FIGS. 2 (I), (II), (III) and (IV) illustrate four general chemical formulas of the substituted 4,5,6,7-tetrahydro-1-benzothiophene ring of the compounds of the present disclosure.
Figure 2:
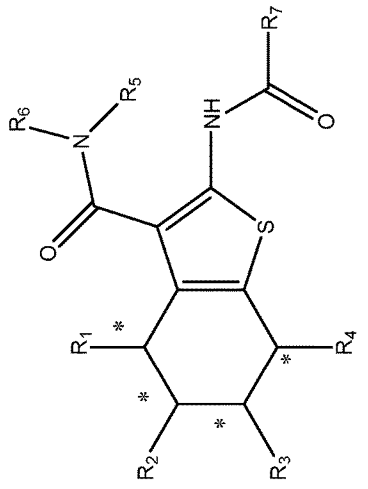
Figure 2:
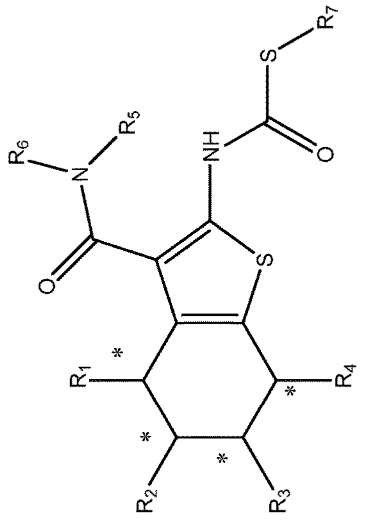
Figure 2:
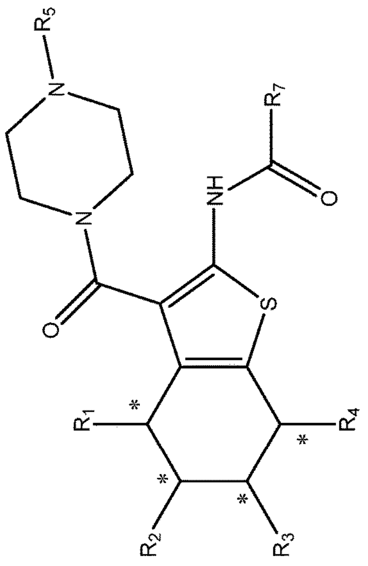

The present disclosure relates to compounds of Formula (I), (II), (III), and (IV) wherein "*" indicate chiral center, as also shown in FIG. 2, along with their pharmaceutically acceptable salts and stereoisomers thereof, which are represented below by the following chemical structures and group definitions:

(I)

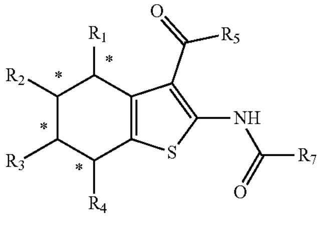

-continued (II)

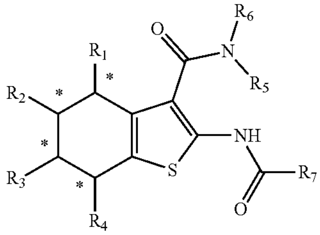

(III)

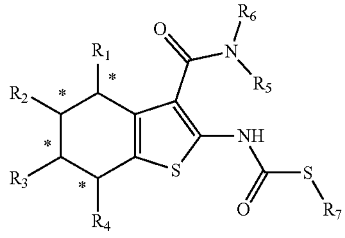

(IV)

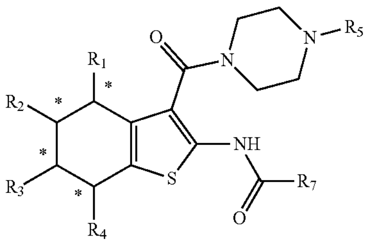

The $R_1$ to $R_7$ groups of the compounds of Formula (I), (II), (III), and (IV) have the following definitions:

the $R_1$, $R_2$, $R_3$, and/or $R_4$ group(s) is/are H, halogen, $NO_2$, 1-6 alkoxy, OH, $NH_2$, 1-6 alkyl, 1-6 alkenyl, 1-6 haloalkyl, N-dialkyl, haloalkoxy, 1-6 hydroxyalkyl, and/or —$CO_2$(1-6 alkyl), the $R_5$ group is a substituted or unsubstituted five or six membered saturated or unsaturated heterocycle, aryl, alkylarene, halo aryl, ring substituted alkylarene, ring substituted alkyl-hexane, ring substituted alkyl-cyclopentane, haloaryl, benzene, benzyl, phenyl, pyridine, pyrimidine, pyridine, imidazole, diazole, triazole, thiadiazole, imidazolidine, thizolidine, pyrrolidine, piperazine, piperidine, pyridazine, pyrazine, triazine, 1H pyrrole, 2H pyrrole, pyrroline, pyrazolidine, pyrazoline, thiazole, isothiazole, isoxazole, haloalkyl, cyanoalkyl, methylpyrimidine, toluene, methylpyridine, methylimidazole, methyldiazole, methyltriazole, methylthiadiazole, methylimidazolidine, methylthizolidine, methylpyrrolidine, methylpiperazine, methylpiperidine, methylpyridazine, methylpyrazine, methyltriazine, methylpyrrole, methylpyrroline, methylpyrazolidine, methylpyrazoline, methylthiazole, methylisothiazole, methylisoxazole, or arylalkyl.

the $R_6$ group is H, 1-6 alkyl, or may form a five or six ring structure with $R_5$; and the $R_7$ group is a substituted or unsubstituted five or six membered saturated or unsaturated heterocycle, ring substituted alkylarene, ring substituted alkyl-hexane, ring substituted alkyl-cyclopentane, substituted haloaryl, substituted benzene, substituted phenyl, benzyl, pyrimidine, pyridine, imidazole, diazole, triazole, thiadiazole, imidazolidine, thizolidine, pyrrolidine, piperazine, aryl, halo aryl, alkylarene, piperidine, pyridazine, pyrazine, triazine, 1H pyrrole, 2H pyrrole, pyrroline, pyrazolidine, pyrazoline, thiazole, isothiazole, isoxazole, cyanoalkyl, methylpyrimidine, toluene, methylpyridine, methylimidazole, methyldiazole, methyltriazole, methylthiadiazole, methylimidazolidine, methylthizolidine, methylpyrrolidine, methylpiperazine, methylpiperidine, methylpyridazine, methylpyrazine, methyltriazine, methylpyrrole, methylpyrroline, methylpyrazolidine, methylpyrazoline, methylthiazole, methylisothiazole, methylisoxazole, or arylalkyl.

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also be useful. Inactive or less active diastereoisomers and enantiomers are useful for scientific studies relating to the nuclear receptor targeting and the mechanism of activation.

The compounds disclosed herein may be used in pharmaceutical compositions comprising: (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound of Formula (I), (II), (III), and (IV) or a pharmaceutically acceptable salt thereof is the only active ingredient.

According to an embodiment, the compounds are modulators of RORα and RORγt and are useful for the control of autoimmune diseases and antibody mediated rejection. Such compounds may be useful in the treatment of autoimmune disease and antibody mediated rejection and may also be useful in the treatment of other RORγt-mediated diseases or conditions.

According to another embodiment, the compounds may be given directly to a patient in need of such treatment, using oral, intravenous, topical, intranasal, intrapulmonary, subcutaneous (slow release implant or patch), sublingual, inhalation, or intramuscular administration.

ROR alpha and RORγt are both expressed in lymphocytes during maturation. Irregularities in the expressions of ROR genes may lead to cancer, autoimmune disease. RORγt is the master regulator is Th17. Th17 cells produce many proinflammatory and pleiotropic cytokines IL17A, IL17F (can be also anti-inflammatory), IL21, IL22, IL24, IL26. In addition, Th17 cells secrete GM-CSF and TNF alpha. T cytotoxic 17 is also a type of lymphocyte that secrete all the aforementioned cytokines. T follicular helper cells secrete IL21 and are involved in many inflammatory diseases and types of cancers.

The compounds bind to ROR alpha and ROR gamma and block the production of IL17A, IL21, IL17F, IL24, IL26 and other cytokines produced by either T helper 17, T cytotoxic 17, T follicular helper cells, and those produced by all variants or cytotoxic T cells, and Helper T cells as well as variants of B cells that produce the aforementioned cytokines.

Th17 cells have a role in macrophage and leukocytes recruitment to cause inflammation. RORC and RORA are highly expressed in certain types of cancer and in autoimmune diseases. Patients waitlisted on organ transplantation lists and who are categorized as highly sensitized patients have a high activity of T helper 17, T follicular cells, and all T cell variants that produce the aforementioned cytokines. The invention would confer a therapeutic benefit to this category and to all other people who receive allogenic transplantation.

The compounds are useful in treatment of diseases involving the immune system whenever any of the aforementioned cytokines is involved either directly or indirectly in the activation of the immune system. The compounds are useful in treatment of cancers involving blood, liver, breast, gastrointestinal tract.

Types of autoimmune diseases that may be treated by compounds include, but are not limited to, cancer, celiac disease, diabetes mellitus type 1, Graves' disease, inflammatory bowel disease, multiple sclerosis, psoriasis, rheumatoid arthritis, systemic lupus erythematosus, asthma, dermatitis, fatty liver disease, Crohn's disease, cardiovascular disease, inflammatory diseases, neurological disorder, multiple sclerosis and arteriosclerosis.

Types of cancer that may be treated by compounds include, but are not limited to, prostate cancer, breast cancer, brain cancer, glioma, lung cancer, salivary cancer, stomach cancer, thymic epithelial cancer, thyroid cancer, ovarian cancer, multiple myeloma, leukemia, melanoma, lymphoma, gastric cancer, kidney cancer, pancreatic cancer, bladder cancer, colon cancer and liver cancer.

Compounds may be useful in treatment of diseases and conditions characterized by increased, decreased, irregular, or dysregulated expression of RORγt, RORγ, RORα and their products such as IL17, IL21, IL22, IL24, IL26 and other gene products that are regulated by ROREs.

RORC-Associated Diseases

Acromegaly, rheumatoid arthritis, malignant neoplasm of breast, candidiasis, hypertrophic, cardiomyopathy, colorectal carcinoma, Crohn's disease, diabetes, diabetes mellitus, non-insulin-dependent diabetes mellitus, hamartoma, inflammatory bowel diseases, *mycobacterium* infections, systemic scleroderma, tuberous sclerosis, joint swelling, lobomycosis, hepatitis, autoimmune malignant neoplasm of lung, growth hormone-secreting pituitary adenoma, pre B-cell acute lymphoblastic leukemia, malignant neoplasm of prostate, prostate carcinoma, breast carcinoma, carcinoma of lung, familial multiple trichoepitheliomata, primary malignant neoplasm of lung, colorectal cancer, Friedreich ataxia 1, allergic rhinitis (disorder), pachyonychia congenita 3, early rheumatoid arthritis, necrotizing enterocolitis in fetus or newborn, autoimmune diseases, Roberts-sc phocomelia syndrome, dysfunction—skin disorders, obesity, lymphedema, tobacco use disorder, inflammation, sleep disorders, circadian rhythm, immunodeficiency-42, antibody mediated rejection, acute solid organ transplant rejection (liver, heart, lung, kidneys), chronic solid organ graft rejection (liver, heart, lung, kidneys), alloimmune hypersensitivity.

RORA-Associated Diseases

Bipolar disorder, mental depression, depressive disorder, autistic disorder, stomach neoplasms, seasonal affective disorder, anoxia, age related macular degeneration, atherosclerosis, choriocarcinoma, dyslipidemias, tobacco use disorder, choroidal neovascularization, sleep disorders, major depressive disorder, carcinogenesis, liver carcinoma, bone diseases, malignant neoplasm of breast, malignant tumor of colon, colitis, epithelial cyst, hepatitis B, hypothyroidism, liver diseases, liver neoplasms, metabolic diseases, neuroblastoma, degenerative polyarthritis, osteoporosis, dermatologic disorders, post-traumatic stress disorder, liver failure, depressive symptoms, complete atrioventricular block, chronic, breast carcinoma, colon carcinoma, central neuroblastoma, atrophy of cerebellum, adenoviral infections, autism spectrum disorders, steatohepatitis, acute-on-chronic liver failure, antibody mediated rejection, acute solid organ transplant rejection (liver, heart, lung, kidneys), chronic solid organ graft rejection (liver, heart, lung, kidneys), alloimmune hypersensitivity.

IL17A-Associated Diseases

Antibody mediated rejection, acute solid organ transplant rejection (liver, heart, lung, kidneys), chronic solid organ graft rejection (liver, heart, lung, kidneys), alloimmune hypersensitivity, arthritis, experimental, autoimmune diseases, inflammation, colitis, pneumonia, hypersensitivity, graft-vs-host disease, brain ischemia, chronic alcoholic intoxication, CNS disorder, acute promyelocytic leukemia, lymphoproliferative disorders, necrosis, alcohol abuse, chemical and drug induced liver injury, chemical and drug induced liver injury, periodontal diseases, chronic obstructive airway disease, spondylarthrosis, myocardial infarction, diabetes mellitus, hyperalgesia, myocardial reperfusion injury, lipoid nephrosis, pleurisy, pulmonary fibrosis, staphylococcal skin infections, acute necrotizing pancreatitis, anti-glomerular basement membrane disease, rheumatoid arthritis, asthma, psoriasis, arthritis, systemic lupus erythematosus, periodontitis, multiple sclerosis, encephalomyelitis, ulcerative colitis, degenerative polyarthritis, inflammatory bowel diseases, inflammatory bowel diseases, Behcet syndrome, malignant neoplasm of stomach, gingivitis, Sjogren's syndrome, juvenile arthritis, candidiasis, chronic mucocutaneous uveitis, *Helicobacter* infections, Crohn's disease, atopic dermatitis, celiac disease, systemic scleroderma, dermatitis, cutaneous T-cell lymphoma, malignant neoplasm of breast, carcinogenesis, stomach carcinoma, multiple myeloma, Job syndrome, arteriosclerosis, colorectal carcinoma, colorectal cancer, inflammatory dermatosis, bronchiolitis obliterans, keratitis, coronary artery disease, bronchiolitis, cystic fibrosis, rheumatoid nodule, respiratory syncytial virus infections, bone diseases, dyspepsia, endometriosis, alcoholic hepatitis, bone necrosis, rhinitis, thrombocytopenic purpura, ovarian neoplasm, infection, psoriatic arthritis, viral bronchiolitis, stomach neoplasms, tobacco use disorder, mycoses, lupus erythematosus, eczema, lupus vulgaris, lupus erythematosus, discoid virus diseases, bone destruction, capillary malformation (disorder), liver carcinoma, neutrophilia (disorder), diabetes mellitus insulin-dependent, neoplasm metastasis, neoplasm metastasis, dermatologic disorders, ankylosing spondylitis, tuberculosis, liver fibrosis, pneumonitis, bacterial infections, non-small cell lung carcinoma, eosinophilia, lupus nephritis, osteopenia, allergic asthma, malignant neoplasm of lung, cervix carcinoma, superficial ulcer, breast carcinoma, carcinoma of lung, inflammatory disorder, primary malignant neoplasm of lung, eosinophilic disorder, dysfunction—skin disorders, skin erosion, candidiasis, mucocutaneous candidiasis, malignant tumor of colon, malignant tumor of cervix, histiocytosis Langerhans-cell, lung neoplasms, primary Sjogren's syndrome, age related macular degeneration, sepsis, psoriasiform eczema, chronic periodontitis, persistent embryonic structure, *Helicobacter pylori* (*h. pylori*) infection, hepatitis B chronic, colon carcinoma, cervical cancer, refractory anemias, primary biliary cirrhosis, dermatomyositis, diabetes, diabetes mellitus, encephalitis (St. Louis), hepatitis B, influenza, chronic lymphocytic leukemia, mucocutaneous lymph node syndrome, *mycobacterium* infections, nasal polyps, septicemia, ocular toxoplasmosis, Chagas disease, pulmonary tuberculosis, uveomeningoencephalitic syndrome, polyglandular type 1 autoimmune syndrome, complete atrioventricular block, tumor progression, chronic small plaque psoriasis, hyperactive behavior, Hashimoto disease, infectious disease of lung, acute coronary syndrome, mammary neoplasms, tumor, angiogenesis, allergic rhinitis (disorder), autoimmune arthritis, adenoma, alveolar bone loss, extrinsic allergic alveolitis, Alzheimer's disease, bacterial pneumonia, dengue fever, fatty liver, gastritis, glioblastoma, glioma, glomerulonephritis, grave's disease, hamartoma syndrome (multiple), hepatitis, hepatitis A, hypertensive disease, arthropathy, liver cirrhosis, mycosis fungoides, obesity, ovarian carcinoma, pelvic pain, peritonitis, prune belly syndrome, cerebrovascular accident, giant cell arteritis, ulcer, vitiligo, corneal pannus, acute myocardial infarction, abdominal aortic aneurysm, Lyme arthritis, parasitemia, psoriasis vulgaris, mrsa—methicillin resistant *Staphylococcus aureus* infection, respiratory syncytial virus (rsv) infection, acute anterior uveitis, neurological disability, pelvic pain female, acute GVH disease, malignant neoplasm of ovary, fungal keratitis, chronic inflammatory disorder, tumor immunity, painful bladder syndrome, vitiligo-associated multiple autoimmune disease susceptibility 1 (finding), steatohepatitis, ischemic cerebrovascular accident, autoimmune polyendocrinopathy syndrome type 1, interstitial lung fibrosis, acne vulgaris, acquired immunodeficiency syndrome, amyotrophic lateral sclerosis, anemia, aneurysm, Barrett esophagus, malignant neoplasm of urinary bladder, bladder neoplasm, bronchiectasis, brucellosis, oral candidiasis, malignant neoplasm of endometrium, squamous cell carcinoma, cardiovascular diseases, intracranial aneurysm, uterine cervical neoplasm, colonic diseases, colonic neoplasms, common variable immunodeficiency, allergic conjunctivitis, corneal diseases, coronary arteriosclerosis, coronary heart disease, Dejerine-Sottas disease (disorder) delirium, diabetes mellitus, non-insulin-dependent, diabetic nephropathy, enterovirus infections, epilepsy, epithelial hyperplasia, eye infections, giant cell tumors, gonorrhea, chronic granulomatous disease, Guillain-Barre syndrome, cardiac arrest, severe dengue, chronic hepatitis, hepatitis C, herpes simplex infections, herpesviridae infections, HIV infections, Hodgkin disease, hyperlipidemia, hypothyroidism, immune system diseases, kidney diseases, acute kidney failure, chronic kidney failure, leishmaniasis, cutaneous leishmaniasis, infection by *Leishmania braziliensis*, visceral leishmaniasis, leprosy, lepromatous, chronic myeloid leukemia, liver diseases, alcoholic liver diseases, Lyme disease, lymphoma, malaria, cerebral malaria, Marinesco-Sjogren syndrome, melanoma, mitral valve stenosis, myocarditis, nervous system disorder, nodule, osteosarcoma, pain, pustulosis of palms and soles, panuveitis, periodontitis (juvenile), pituitary adenoma, pneumococcal infections, polyps, prostatitis, pulmonary eosinophilia, Henoch-Schoenlein purpura, adult respiratory distress syndrome, retroviridae infections, *salmonella* infections, sarcoidosis, pulmonary sarcoidosis, schizophrenia, Sezary syndrome, situs *inversus*, gastric ulcer, synovitis, thrombocytopenia, thymoma, thyroid diseases, trachoma, tuberous sclerosis, urticaria, anterior uveitis, intermediate uveitis, vaccinia, vascular diseases, vasculitis, intestinal *volvulus*, malignant pleural effusion, adult-onset still disease, autoimmune polyendocrinopathies, liver failure, chronic sinusitis, deep vein thrombosis, chronic pain, active tuberculosis, secondary Sjogren's syndrome, adenocarcinoma of lung (disorder), lobomycosis, pustular psoriasis, systemic candidiasis, acute myocarditis, intervertebral disc disorder, adrenoleukodystrophy, allergic contact dermatitis, hypopigmentation disorder, autoimmune thyroid disease, autoimmune diabetes, interstitial lung diseases, idiopathic hypereosinophilic syndrome, ki-1+ anaplastic large cell lymphoma, hemangioma of liver, papillary thyroid carcinoma, ankle arthritis, autoimmune hepatitis, Lewis lung carcinoma, chronic urticaria, epithelial hyperplasia of skin, childhood asthma, congenital emphysema, infantile colic, typhlocolitis, acquired aplastic anemia, viral myocarditis, rhinovirus infection, infection by *Candida albicans*, gastric adenocarcinoma, tumor necrosis, secondary bacterial pneumonia, asthmatic pulmonary eosinophilia, Lofgrens syndrome, stable angina, anterior myocardial infarction, dissection of aorta, autoimmune enteropathy, generalized pustular psoriasis, malignant neoplasm of prostate, hematologic neoplasms, leukocyte adhesion deficiency type 1, non-alcoholic fatty liver disease, idiopathic crescentic glomerulonephritis, primary antiphospholipid syndrome, endometrial carcinoma, pricking of skin, combined immunodeficiency, central sleep apnea, recurrent tumor, neurodegenerative disorders, X-linked lymphoproliferative disorder, osteosarcoma of bone, aqueous humor disorders, prostate carcinoma, carcinoma of bladder, airway disease, acne, dissecting aneurysm of the thoracic aorta, viral respiratory infection, corneal infection, middle cerebral artery occlusion, acute pneumonia, allergic symptom, type 1 cockayne syndrome, idiopathic inflammatory myopathies, gluten sensitivity, *Helicobacter pylori* infection, arteriopathic disease, *Pseudomonas aeruginosa* infection, endothelial dysfunction, chronic candidiasis, *Plasmodium vivax* infection, mycosis fungoides/Sezary syndrome, chronic graft-versus-host disease, pancolitis, vascular inflammations, invasive ductal breast carcinoma, lymphocytic infiltration, thyroid gland spindle cell tumor with thymus-like differentiation, granulocytosis, pancreatic intraepithelial neoplasia, sporadic breast carcinoma, cardiac fibrosis, familial idiopathic cardiomyopathy, latent tuberculosis, cirrhosis, minimal change nephrotic syndrome, non-neoplastic disorder, severe sepsis, dosage-sensitive sex reversal, chronic myeloproliferative disorder, chronic myeloproliferative disorder with eosinophilia, childhood ataxia with central nervous system hypomyelinization, amyotrophic lateral sclerosis 1, sporadic amyotrophic lateral sclerosis, premature coronary artery disease, type 1 crossed polydactyly, uterine corpus cancer, extranodal NK-T-cell lymphoma, photoreceptor degeneration, chronic Lyme disease, cryopyrin-associated periodic syndromes, chronic kidney disease stage 5, destructive arthritis, adiponectin deficiency, sessile serrated adenoma/polyp, Dianzani autoimmune lymphoproliferative syndrome, autosomal dominant hyper-immunoglobulin e syndrome, immune reconstitution inflammatory syndrome (iris), nonalcoholic steatohepatitis, myelodysplastic syndrome, granulomatosis with polyangiitis, familial hypophosphatemic rickets, allergic disposition, acute-on-chronic liver failure, aspirin exacerbated respiratory disease, pre-renal acute kidney injury, post-treatment Lyme disease syndrome, early rheumatoid arthritis, membranous lupus nephritis, necrotizing enterocolitis in fetus or newborn.

IL21-Associated Diseases

Celiac disease, systemic lupus erythematosus, common variable 11 immunodeficiency, experimental autoimmune encephalomyelitis, periodontal diseases, rheumatoid arthritis, autoimmune diseases, insulin-dependent diabetes mellitus, asthma, ulcerative colitis, Crohn's disease, infection, multiple sclerosis, Sezary syndrome, follicular lymphoma, acquired immunodeficiency syndrome, Hodgkin disease, *falciparum* malaria, juvenile arthritis, chronic lymphocytic leukemia, Addison disease, alopecia areata, viral bronchiolitis, immediate hypersensitivity, respiratory syncytial virus infections, inflammatory bowel diseases, lupus vulgaris, discoid lupus erythematosus, psoriasis, lupus erythematosus, hepatitis B, multiple myeloma, virus diseases, diffuse large B-cell lymphoma, immune thrombocytopenic purpura, complete atrioventricular block, persistent embryonic structure, malignant neoplasm of breast, malignant tumor of colon, colitis, common variable immunodeficiency, atopic dermatitis, diabetes, diabetes mellitus, eczema, Grave's disease, adult T-cell lymphoma/leukemia, lymphoma, malignant neoplasm of stomach, ovarian carcinoma, schistosomiasis, B-cell lymphomas, primary Sjogren's syndrome, chronic hepatitis B, chronic hepatitis C, breast carcinoma, colon carcinoma, stomach carcinoma, malignant neoplasm of ovary, X-linked combined immunodeficiency diseases, pseudohyperkalemia Cardiff, acquired hypogammaglobulinemia, aplastic anemia, arthritis, Burkitt lymphoma, cerebral infarction, echinococcosis, glioblastoma, glioma, graft-vs-host disease, hepatitis, HIV infections, angioimmunoblastic lymphadenopathy, immunologic deficiency syndromes, liver diseases, liver neoplasms, chronic obstructive airway disease, melanoma, Mikulicz disease, nasal polyps, neoplasm metastasis, neuroblastoma, degenerative polyarthritis, polyps, Henoch-Schoenlein purpura, schizophrenia, systemic scleroderma, sialadenitis, cerebrovascular accident, toxoplasmosis, tuberous sclerosis, uveomeningoencephalitic syndrome, cutaneous T-cell lymphoma, severe combined immunodeficiency, Sicca syndrome, oral ulcer, idiopathic pulmonary hypertension, dacryoadenitis, allergic asthma, malnutrition, autoimmune thyroid disease, brain cyst, pancreatic carcinoma, collagenous colitis, bone destruction, autoimmune thrombocytopenia, epithelial hyperplasia of skin, familial lichen amyloidosis, acquired aplastic anemia, thrombocytopenia due to platelet alloimmunization, disseminated neuroblastoma, solid tumor, malignant lymphoma (lymphocytic, intermediate differentiation, diffuse), hematologic neoplasms, lymphocytic colitis, hydatids, thymic alymphoplasia, leukemogenesis, Hashimoto disease, central neuroblastoma, allergic symptom, acute cerebrovascular accidents, pancolitis, cerebral ischemia, ischemic stroke, progressive multiple sclerosis, stage 4s neuroblastoma, inflammatory disorder, ALK negative anaplastic large cell lymphoma, Sjogren's syndrome, benign prostatic hyperplasia, liver carcinoma, idiopathic pulmonary arterial hypertension, ischemic cerebrovascular accident, acute-on-chronic liver failure, early rheumatoid arthritis, selective immunoglobulin a deficiency, antibody mediated rejection, acute solid organ transplant rejection (liver, heart, lung, kidneys), chronic solid organ graft rejection (liver, heart, lung, kidneys), alloimmune hypersensitivity.

IL22-Associated Diseases

Autoimmune hepatitis, middle cerebral artery infractions, chemical and drug induced liver injury, asthma, myocarditis, Crohn's disease, psoriasis, inflammatory bowel diseases, hepatitis C infection, liver carcinoma, autoimmune diseases, rheumatoid arthritis, systemic lupus erythematosus, HIV infections, chronic mucocutaneous candidiasis, pneumonia, inflammation, colitis, ulcerative colitis, viral bronchiolitis, colonic neoplasms, respiratory syncytial virus infections, atopic dermatitis, eczema, chronic lymphocytic leukemia, colon carcinoma, inflammatory dermatosis, malignant tumor of colon, dermatitis, multiple sclerosis, carcinogenesis, celiac disease, malignant neoplasm of stomach, multiple myeloma, primary Sjogren's syndrome, stomach carcinoma, amyloidosis, arthritis, colorectal carcinoma, diabetes mellitus (insulin-dependent), hepatitis A, hepatitis B, liver diseases, liver neoplasms, chronic obstructive airway disease, mycoses, tuberculosis, virus diseases, cutaneous T-cell lymphoma, polyglandular type i autoimmune syndrome, complete atrioventricular block, immune thrombocytopenic purpura, colorectal cancer, dysfunction—skin disorders, bacterial infections, Bechet syndrome, malignant neoplasm of breast, candidiasis, non-small cell lung carcinoma, glioblastoma, grave's disease, lymphoma, ovarian carcinoma, schistosomiasis, Sezary syndrome, dermatologic disorders, uveitis, diffuse large B-cell lymphoma, malnutrition, ki-1+ anaplastic large, cell lymphoma, liver fibrosis, persistent embryonic structure, hyperactive behavior, breast carcinoma, *Helicobacter pylori* infection, malignant neoplasm of ovary, Sjogren's syndrome, acute colitis, abscess, adenocarcinoma, adenovirus infections, Alzheimer's disease, aortic valve insufficiency, bacterial pneumonia, Burkitt lymphoma, oral candidiasis, candidiasis of vagina, squamous cell carcinoma, cerebral infarction, colonic diseases, cytomegalovirus infections, Dejerine-Sottas disease (disorder), dengue fever, diabetes, diabetes mellitus, non-insulin-dependent diabetes mellitus, diarrhea, echinococcosis, erythema nodosum, gastroenteritis, gingival diseases, glioma, graft-vs-host disease, severe dengue, angioimmunoblastic lymphadenopathy, immunologic deficiency syndromes, influenza, leukemia myelocytic, alcoholic liver diseases, lupus vulgarism discoid lupus erythematosus, lupus nephritis, melanoma, nasal polyps, nephritis, neuroblastoma, nodule, obesity, degenerative polyarthritis, pustulosis of palms and soles, pancreatitis, periodontal diseases, polyps, Henoch-Schoenlein purpura, rotavirus infections, schizophrenia, systemic scleroderma, septicemia, skin lesion, ankylosing spondylitis, cerebrovascular accident, thyroid diseases, toxoplasmosis, tuberous sclerosis, urticaria pigmentosa, viral hepatitis, vitiligo, B-cell lymphomas, severe combined immunodeficiency, sicca syndrome, retinal vasculitis, lobomycosis, idiopathic pulmonary hypertension, corneal pannus, hypopigmentation disorder, hidradenitis suppurativa, intestinal infectious disease (disorder), autoimmune thyroid disease, tumor progression, brain cyst, pancreatic carcinoma, collagenous colitis, papillary thyroid carcinoma, malignant neoplasm of lung mucosa-associated lymphoid tissue, lymphoma, sepsis, psoriasiform eczema, psoriasis vulgaris, epithelial hyperplasia of skin, typhlitis, familial lichen amyloidosis, acquired aplastic anemia, disseminated neuroblastoma, capillary malformation (disorder), generalized pustular psoriasis, methicillin resistant *Staphylococcus aureus* (mrsa) infection, *Helicobacter pylori* (h. *pylori*) infection, hematologic neoplasms, microscopic colitis, lymphocytic colitis, proliferative nephritis unspecified, chronic small plaque psoriasis, lupus erythematosus, pricking of skin, hydatids, chronic hepatitis B, chronic hepatitis C, leukemogenesis, Hashimoto disease, carcinoma of lung, central neuroblastoma, acute cerebrovascular accidents, acute GVH disease, cerebral ischemia, intraabdominal infections, stage 4s neuroblastoma, X-linked combined immunodeficiency diseases, inflammatory disorder, chronic inflammatory disorder, primary malignant neoplasm of lung, anaplastic, ALK negative large cell lymphoma, ALK-positive anaplastic large cell lymphoma, gastric mucosa-associated lymphoid tissue lymphoma, intestinal graft versus host disease, benign prostatic hyperplasia, chromosome 11p11.2 deletion syndrome, immune suppression, vitiligo-associated multiple autoimmune disease susceptibility 1, dosage-sensitive sex reversal, peeling skin syndrome, pseudohyperkalemia cardiff, immune reconstitution inflammatory syndrome (iris), idiopathic pulmonary arterial hypertension, enthesitis-related arthritis, ulcerative colitis in remission, pneumonitis, early rheumatoid arthritis. antibody mediated rejection, acute solid organ transplant rejection (liver, heart, lung, kidneys), chronic solid organ graft rejection (liver, heart, lung, kidneys), alloimmune hypersensitivity.

IL24-Associated Disease

Lung neoplasms, pancreatic neoplasm, major depressive disorder, mammary neoplasms, prostatic neoplasms, spontaneous abortion, unipolar depression, periodontal diseases, melanoma, liver carcinoma, glioma, carcinoma of lung, malignant neoplasm of lung, malignant neoplasm of breast, prostate carcinoma, breast carcinoma, primary malignant neoplasm of lung, metastatic melanoma, malignant neoplasm of prostate, glioblastoma, chronic lymphocytic leukemia, squamous cell carcinoma, adenocarcinoma, rheumatoid arthritis, non-small cell lung carcinoma, neoplasm metastasis, asthma, viral bronchiolitis, hepatitis C, HIV infections, respiratory syncytial virus infections, ovarian carcinoma, pancreatic carcinoma, malignant neoplasm of ovary, colorectal carcinoma, malignant neoplasm of pancreas, glioblastoma multiforme, colorectal cancer, leukemia, psoriasis, epithelial ovarian cancer, tumor angiogenesis, renal cell carcinoma, liver and intrahepatic biliary tract carcinoma, solid tumor, malignant neoplasm of liver, malignant glioma, renal carcinoma, autoimmune diseases, ulcerative colitis, Crohn's disease, inflammatory bowel diseases, influenza, acute lymphocytic, leukemia, myeloid leukemia, retinoblastoma, secondary malignant neoplasm of lung, carcinogenesis, stomach carcinoma, ovarian neoplasm, dysfunction—skin disorders, malignant neoplasm of urinary bladder, bladder neoplasm, brain neoplasms, malignant tumor of colon, malignant tumor of cervix, dermatitis, lymphoid leukemia, acute myelocytic leukemia, systemic lupus erythematosus, malignant neoplasm of stomach, mesothelioma, experimental neoplasms, neuroblastoma, pustulosis of palms and soles, juvenile periodontitis, *salmonella* infections, dermatologic disorders, typhoid fever, urinary tract infection, virus diseases, vitiligo, tumor progression, acute urinary tract infection, epithelial hyperplasia of skin, gastric adenocarcinoma, conventional (clear cell) renal cell carcinoma, cervix carcinoma, generalized pustular psoriasis, malignant mesothelioma, multiple malignancy, disseminated malignant neoplasm, neuropathy, squamous cell carcinoma of skin, secondary malignant neoplasm of lymph node, colon carcinoma, carcinoma of bladder, central neuroblastoma, microphthalmia (syndromic 7), malignant pleural mesothelioma, adenoviral infections, B lymphoblastic leukemia/lymphoma, squamous cell carcinoma of the head and neck, mesothelioma (malignant, clinical disorder) (disorder), pancreatic ductal adenocarcinoma, mammary tumorigenesis, vitiligo-associated multiple autoimmune disease susceptibility 1, precursor cell, lymphoblastic leukemia lymphoma, mechanical allodynia, inflammatory dermatosis, mixed lineage leukemia, persistent oligoarticular juvenile idiopathic arthritis, cervical cancer.

IL26-Associated Diseases

Rheumatoid arthritis, Crohn's disease, asthma, viral bronchiolitis, ulcerative colitis, insulin-dependent diabetes mellitus, inflammatory bowel diseases, multiple sclerosis, respiratory syncytial virus infections, tobacco use disorder, chronic ulcerative colitis, bronchiolitis obliterans, graft-vs-host disease, malignant neoplasm of stomach, pulmonary fibrosis, tuberculosis, stomach carcinoma, chronic graft-versus-host disease.

Abbreviations

Abbreviations and terms that are commonly used in the fields of organic chemistry, medicinal chemistry, pharmacology, and medicine and are well known to practitioners in these fields are used herein. Representative abbreviations and definitions are provided below:

Ac is acetyl [$CH_3C(O)$—], $Ac_2O$ is acetic anhydride; APC is antigen-presenting cell; 9-BBN is 9-borabicyclo[3.3.1] nonane; Bn is benzyl; BOC is tert Butyloxycarbonyl; DIAD is diisopropylazodicarboxylate; DIBAL is diisobutylaluminum hydride; DMF is N,N-dimethylformamide; DMSO is dimethyl sulfoxide; EDAC (or EDC) is 1-ethyl-3-[3-(dimethylamino)propyl]-carbodiimide HCl; $Et_3N$ is triethylamine; Et is ethyl; EtOAc is ethyl acetate; EtOH is ethanol; 3-F-Ph is 3-fluorophenyl, HCl is hydrochloric acid; HOBt is 1-hydroxybenzotriazole; HPLC is high performance liquid chromatography; LCMS is HPLC with mass spectral detection; LG is leaving group; M is molar; mmol is millimole; Me is methyl; MeOH is methanol; MsCl methanesulfonyl chloride; NaHMDS is sodium hexamethyldisiliazide; NaOAc is sodium acetate; NaOtBu is sodium tert-butoxide; NMO is N-methylmorpholine N oxide; NMP is N Methyl pyrrolidinone; $Pd(dba)_2$ is tris(dibenzylideneacetone)dipalladium; $PdCl_2(Ph_3P)_2$ is dichlorobis-(triphenylphosphene) palladium; PG denotes an unspecified protecting group; PCC is pyridinium chlorochromate; POCl3 is phosphorus oxychloride; Ph is phenyl; PhMe is toluene; $PPh_3$ is triphenylphosphine; PMB is para-methoxybenzyl; RT is room temperature; TBAF is tetrabutyl ammonium fluoride; TBS is tert-butyldimethylsilyl; tBu is tert-butyl; Tf is triflate; TFA is trifluoroacetic acid; THF is tetrahydrofuran; TLC is thin layer chromatography; TMAO is trimethylamine oxide; DMF is dimethylformamide; TMS is trimethylsilyl; TPAP is tetrapropylammonium perruthenate.

Definitions

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from C3-10, the term alkyl also includes cycloalkyl groups, and combinations of linear or branched alkyl chains combined with cycloalkyl structures. When no number of carbon atoms is specified, C1-6 is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to unbranched or branched chain alkoxides of the number of carbon atoms specified (e.g., C1-6 alkoxy), or any number within this range [i.e., methoxy (MeO—), ethoxy, isopropoxy, etc.]

The term "alkylthio" refers to unbranched or branched chain alkylsulfides of the number of carbon atoms specified (e.g., C1-6 alkylthio), or any number within this range [i.e., methylthio (MeS—), ethylthio, isopropylthio, etc.]

The term "alkylamino" refers to unbranched or branched alkylamines of the number of carbon atoms specified (e.g., C1-6 alkylamino), or any number within this range [i.e., methylamino, ethylamino, isopropylamino, t-butylamino, etc.]

The term "alkylsulfonyl" refers to unbranched or branched chain alkylsulfones of the number of carbon atoms specified (e.g., C1-6 alkylsulfonyl), or any number within this range [i.e., methylsulfonyl ($MeSO_2^-$), ethylsulfonyl, isopropylsulfonyl, etc.]

The term "alkylsulfinyl" refers to unbranched or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.]

The term "alkyloxycarbonyl" refers to unbranched or branched chain esters of a carboxylic acid derivative of the number of carbon atoms specified (e.g., $C_{1-6}$ alkyloxycarbonyl), or any number within this range [i.e., methyloxycarbonyl ($MeOCO^-$), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, 2-oxoazetidin-1-yl, 1,2,4-oxadiazin-5(6H)-one-3-yl, and the like.

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term «composition» as used herein is intended to encompass a product comprising the specified ingredients in the specified amounts, as well as any product which results, directly or indirectly, from combination of the specified ingredients in the specified amounts. Such term in relation to pharmaceutical composition is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions encompass any composition made by admixing a compound and a pharmaceutically acceptable carrier. By "pharmaceutically acceptable" or "acceptable" it is meant the carrier, diluent or excipient must be compatible with the other ingredients of the formulation and not deleterious to the recipient thereof.

Compounds of structural Formula (I), (II), (III), and (IV) may contain one or more asymmetric centers and can thus occur as racemates and racemic mixtures, single enantiomers, diastereomeric mixtures and individual diastereomers. The compounds are meant to comprehend all such isomeric forms of the compounds of structural Formula (I), (II), (III), and (IV).

Compounds of structural Formula (I), (II), (III), and (IV) may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural Formula (I), (II), (III), and (IV) may be obtained by stereospecific synthesis using optically pure starting materials or reagents of known absolute configuration.

FIGS. 3A-B, 4A-B, 5A-B, and 6A-B illustrate the synthesis of the compounds represented by the general formula (I), (II), (III), and (IV).

FIGS. 3A-B, 4A-B, 5A-B, and 6A-B illustrate the synthesis of the compounds 1 to 23 and chemical analogues presented by the general formula (I), (II), (III), and (IV). The compounds synthetized and disclosed herein comprises 23 compounds which, according to the International Union of Pure and Applied Chemistry (IUPAC) nomenclature, are named:

Compound 1: N-(3-(4-benzylpiperazine-1-carbonyl)-4,5,6,7-tetrahydro-benzo[b]thiophen-2-yl)-2-fluorobenzamide;

Compound 2: N-(3-(benzylcarbamoyl)-4,5,6,7-tetrahydrobenzo[b]thiophen-2-yl)-5-chloro-2-(methylthio)pyrimidine-4-carboxamide;

Compound 3: 5-chloro-N-(3-{[(1,1-dioxidotetrahydro-3-thienyl)amino]-carbonyl}-6-methyl-4,5,6,7-tetrahydro-1-benzothien-2-yl)-2-(methylthio)-4-pyrimidine-carboxamide;

Compound 4: N-(6-ethyl-3-{[(2-methylphenyl)amino]carbonyl}-4,5,6,7-tetrahydro-1-benzothien-2-yl)-1-methyl-1H-pyrazole-5-carboxamide;

Compound 5: N-{6-tert-butyl-3-[(4-methyl-1-piperazinyl)carbonyl]-4,5,6,7-tetrahydro-1-benzothien-2-yl}-2-fluorobenzamide;

Compound 6: 2-fluoro-N-{6-methyl-3-[(4-methyl-1-piperazinyl)carbonyl]-4,5,6,7-tetrahydro-1-benzothien-2-yl}benzamide;

Compound 7: N-benzyl-2-[(trifluoroacetyl)amino]-4,5,6,7-tetrahydro-1-benzothiophene-3-carboxamide;

Compound 8: N-benzyl-2-({[(4-methyl-2-pyrimidinyl)thio]acetyl}amino)-4,5,6,7-tetrahydro-1-benzothiophene-3-carboxamide;

Compound 9: N-benzyl-2-[(1-piperidinylacetyl)amino]-4,5,6,7-tetrahydro-1-benzothiophene-3-carboxamide;

Compound 10: N-benzyl-2-{[(4-methyl-1-piperazinyl)acetyl]amino}-4,5,6,7-tetrahydro-1-benzothiophene-3-carboxamide;

Compound 11: N-benzyl-2-{[(4-methyl-1-piperidinyl)acetyl]amino}-4,5,6,7-tetrahydro-1-benzothiophene-3-carboxamide;

Compound 12: N-(3-(2-methylpyrrolidine-1-carbonyl)-4,5,6,7-tetrahydro-benzo[b]thiophen-2-yl)nicotinamide;

Compound 13: N-(3-((2R,4R)-2,4-dimethylpiperidine-1-carbonyl)-4,5,6,7-tetrahydrobenzo[b]thiophen-2-yl)nicotinamide;

Compound 14: N-(3-(((1r,4r)-4-hydroxycyclohexyl)carbamoyl)-4,5,6,7-tetrahydrobenzo[b]thiophen-2-yl)nicotinamide;

Compound 15: N-(3-(3-ethylpyrrolidine-1-carbonyl)-4,5,6,7-tetrahydro-benzo[b]thiophen-2-yl)nicotinamide;

Compound 16: N-benzyl-2-(2-((1-methyl-1H-imidazol-2-yl)thio)acetamido)-4,5,6,7-tetrahydrobenzo[b]thiophene-3-carboxamide;

Compound 17: N-(3-(3-(hydroxymethyl)pyrrolidine-1-carbonyl)-4,5,6,7-tetrahydrobenzo[b]thiophen-2-yl)nicotinamide;

Compound 18: N-(6,6-dimethyl-3-(morpholine-4-carbonyl)-4,5,6,7-tetrahydrobenzo[b]thiophen-2-yl)pyrazine-2-carboxamide;

Compound 19: N-(3-(((1-methyl-1H-1,2,4-triazol-3-yl)methyl)carbamoyl)-4,5,6,7-tetrahydrobenzo[b]thiophen-2-yl)nicotinamide;

Compound 20: (S)—N-(3-((1-cyanoethyl)carbamoyl)-4,5,6,7-tetrahydro-benzo[b]thiophen-2-yl)nicotinamide;

Compound 21: N-(3-((piperidin-4-ylmethyl)carbamoyl)-4,5,6,7-tetrahydro-benzo[b]thiophen-2-yl)nicotinamide;

Compound 22: N-(3-benzoyl-4,5,6,7-tetrahydrobenzo[b]thiophen-2-yl)pyrazine-2-carboxamide; and Compound 23: N-(3-benzoyl-4,5,6,7-tetrahydrobenzo[b]thiophen-2-yl)-5-methyl-2-(methylsulfonyl)pyrimidine-4-carboxamide.

Particularly, compounds 1 to 23 may be in the form of a pharmaceutically acceptable salts. Pharmaceutically acceptable salts and common methodology for preparing them are well known in the art. (e.g., P. Stahl, et al. Handbook of Pharmaceutical Salts—Properties, Selection and Use, $2^{nd}$ Revised Edition (Wiley-VCH, 2011); S. M. Berge, et al., Pharmaceutical Salts, Journal of Pharmaceutical Sciences, Vol. 66, No. 1, January 1977).

The skilled artisan will appreciate that compounds represented by the Formula (I), (II), (III), and (IV) or pharmaceutically acceptable salt thereof, may contain four chiral centers, as represented by "*" in FIG. 2. In addition, some chiral centers may arise in situations where the $R_1$-$R_7$ groups contains additional chiral centers. The compounds 1 to 23 disclosed herein contemplate all individual enantiomers, as well as mixtures of the enantiomers of said compounds, including racemates. The skilled artisan will also appreciate that the Cahn Ingold-Prelog (R) or (S) designations for all chiral centers will vary depending upon the substitution patterns of a particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds 1 to 23 and compounds represented by the general formulas (I), (II), (III), and (IV). Single enantiomers of compounds 1 to 23 and compounds represented by the general formula (I), (II), (III), and (IV) disclosed herein are a preferred embodiment. Also, compounds 1 to 23 and compounds represented by the general formula (I), (II), (III), and (IV) are preferably formulated as pharmaceutical compositions administered by a variety of routes. Such pharmaceutical compositions and processes for preparing the same are well known in the art (i.e. A. Gennaro, et al., Remington: The Science and Practice of Pharmacy, $21^{st}$ ed., Mack Publishing Co., 2005). More particularly preferred, is a pharmaceutical composition comprising a compound of the Formula (I), (II), (III), or (IV).

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds.

In the compounds of generic Formula (I), (II), (III), and (IV) the atoms may exhibit their natural isotopic abundances, or one or more of the atoms may be artificially enriched in a particular isotope having the same atomic number, but an atomic mass or mass number different from the atomic mass or mass number predominantly found in nature. The compounds are meant to include all suitable isotopic variations of the compounds of generic Formula (I), (II), (III), and (IV). For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I), (II), (III), and (IV) can be prepared without undue experimentation by conventional techniques well known to those skilled in the art or by processes analogous to those described in the Schemes and Examples herein using appropriate isotopically-enriched reagents and/or intermediates.

Salts and Formulations

It will be understood that, as used herein, references to the compounds of structural Formula (I), (II), (III) and (IV) are meant to also include the pharmaceutically acceptable salts, and also salts that are not pharmaceutically acceptable when they are used as precursors to the free compounds or their pharmaceutically acceptable salts or in other synthetic manipulations. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds which are generally prepared by reacting the free base with a suitable organic or inorganic acid. Representative salts of basic compounds include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid or alcohol group being present in the compounds, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural Formula (I), (II), (III) and (IV) are included as well.

According to an embodiment, the compounds of structural Formula (I), (II), (III), and (IV) may be included in various formulations for use as medicaments. Formulations for oral use may be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns).

This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from approx. 1 mg to approx. 20 mg of the compound per actuation and the actuation volume may vary from approx. 1 microliter to approx. 1000 microliters. A typical formulation may comprise a compound of Formula (I), (II), (III), and (IV), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release using, for example, poly(D,L-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units are typically arranged to administer a metered dose or "puff" containing from 1 ng to 10 mg of the compound of Formula (I), (II), (III), and (IV). The overall daily dose will typically be in the range 1 ng to 10 mg which may be administered in a single dose or, more usually, as divided doses throughout the day.

All the molecules are effective starting at nano molar concentrations and they do not cause cell death in culture in high micro-molar concentrations.

Compounds of Formula (I), (II), (III), and (IV) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula (I), (II), (III, and (IV) are employed. For purposes of this application, topical application shall include mouth washes and gargles.

Utilities

The compounds specifically exemplified herein exhibit good efficacy in modulating RORγt, as shown by their in vitro assays.

According to an embodiment, the inhibitors of RORγt may improve and may have utility in preventing or treating autoimmune diseases.

One aspect provides a method for the treatment and control of cancer, which comprises administering to a patient in need of such treatment a therapeutically effective amount of a compound of Formula (I), (II), (III), and (IV) and an anticancer agent.

In addition to primates, such as humans, a variety of other mammals can be treated according to the method. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g. chickens).

Combination Therapy

A patient in need of immunotherapy may be treated with antigen-presenting cell (APCs) activated with a compound of Formula (I), (II), (III), and (IV) contemporaneously with other treatments known to the medical practitioner. The use of such multiple treatments may be particularly advantageous to the patient. Such treatments may include, but are not limited to, surgical resection, radiation, chemotherapy, targeted therapy and other types of immunotherapy. Chemotherapy agents that may be used include:

a) cytotoxic agents such as taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof,
b) antimetabolites such as methotrexate, 6-mercaptopurine, 6-thioguanine, cytarabine, 5-fluorouracil decarbazine;
c) alkylating agents such as mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin;
d) anthracyclines such as daunorubicin and doxorubicin;
e) antibiotics such as dactinomycin, bleomycin, mithramycin, and anthramycin (AMC);
f) anti-mitotic agents such as vincristine and vinblastine;
g) targeted therapies that may be used include, but they are not limited to: hormone therapies (such as degarelix, a luteinizing hormone-releasing hormone (LHRH) antagonist that reduces testosterone levels in prostate cancer), signal transduction inhibitors (such as imatinib and trastuzumab), as well as gene expression modulators (e.g. HDAC inhibitors panobinostat and belinostat), apoptosis inducers (e.g. recombinant human TNF-related apoptosis-inducing ligand (TRAIL)) and angiogenesis inhibitors (such as sorafenib, sunitinib, pazopanib, and everolimus); and
h) immunotherapy agents that may be used include: monoclonal antibodies treatment (anti-CTLA4, anti-PD1), and chimeric antigen receptors (CARs) T-Cells.

The following Examples are provided to illustrate the invention and are not to be construed as limiting the invention in any manner. The scope of the invention is defined by the appended claims.

Example 1

Chemical Synthesis

The novel RORs modulators of Formula (I), (II), (III) and (IV) represented by compounds 1 to 23 may be synthetized according to FIGS. 3A-B, 4A-B, 5A-B, and 6A-B or, alternatively, by combinatorial chemistry.

FIG. 3A illustrates a formylation reaction of 2-amino-4,5,6,7-tetrahydro-1-benzothiophene reactant. In this case, the 2-amino-4,5,6,7-tetrahydro-1-benzothiophene is substituted at position three with a formaldehyde group. This is followed by a ketone formation reaction between the aldehyde moiety of 3 substituted 2-amino-4,5,6,7-tetrahydro-1-benzothiophene and Grignard reagent coupled to $R_5$ group. The resulting ketone derivative is isolated and purified by chromatography.

FIG. 3B illustrates a coupling reaction between 3-keto-2-amino-4,5,6,7-tetrahydro-1-benzothiophene and a reactant bearing a $R_7$ group. In this case, the 2-amino group of the substituted 2-amino-4,5,6,7-tetrahydro-1-benzothiophene is coupled with an acyl chloride derivative bearing the $R_7$ group to form an amide bond. The final product can then be isolated chromatography.

Particularly, in the reaction illustrated in FIG. 3B shows the preparation of compounds of the general formula (I) illustrated in FIG. 2, the 3-keto-2-amino-4,5,6,7-tetrahydro-1-benzothiophene (substituted with groups $R_1$-$R_5$ in the defined positions as illustrated) is dissolved in aqueous NaOH and the acyl chloride derivative is dissolved in ether. The 3-keto-2-amino-4,5,6,7-tetrahydro-1-benzothiophene (substituted with groups $R_1$-$R_5$ in the defined positions as illustrated) is added to a conical flask and the acyl chloride derivative is added dropwise to the aqueous solution overnight at 20° C. The resulting mixture is purified by chromatography to isolate compounds of formula.

FIG. 4A illustrates a one-pot substitution reaction of 2-amino-4,5,6,7-tetrahydro-1-benzothiophene reactant, POCl3, DMF, and secondary amine bearing $R_5$ and $R_6$ groups. In this case, the 2-amino-4,5,6,7-tetrahydro-1-benzothiophene is substituted at position 3 by amido coupled to $R_5$ group. The resulting compound is then isolated by chromatography.

FIG. 4B illustrates a coupling reaction between 3-amido 2-amino-4,5,6,7-tetrahydro-1-benzothiophene and a reactant bearing a $R_7$ group. In this case, the 2-amino group of the substituted 2-amino-4,5,6,7-tetrahydro-1-benzothiophene is coupled with an acyl chloride derivative bearing the $R_7$ group to form an amide bond. The final product can then be isolated chromatography.

Particularly, in the reaction illustrated in FIG. 4B shows the preparation of compounds of the general formula (II) illustrated in FIG. 2, the 3-amido-2-amino-4,5,6,7-tetrahydro-1-benzothiophene substituted with groups $R_1$-$R_6$ in the defined positions as illustrated) is dissolved in aqueous NaOH and the acyl chloride derivative is dissolved in ether. The 3-amido-2-amino-4,5,6,7-tetrahydro-1-benzothiophene (substituted with groups $R_1$-$R_6$ in the defined positions as illustrated) is added to an Erlenmeyer flask and the acyl chloride derivative is added dropwise to the aqueous solution overnight at 20° C. The resulting mixture is purified by chromatography to isolate compounds of formula.

FIG. 5A illustrates a one-pot substitution reaction of 2-amino-4,5,6,7-tetrahydro-1-benzothiophenering. Similar to the reaction shown in FIG. 4A, the 2-amino-4,5,6,7-tetrahydro-1-benzothiophene is substituted at position 3 by amido coupled to $R_5$ group. The resulting compound is then isolated by chromatography.

FIG. 5B illustrates two steps of preparation of compounds represented by the general formula (III). The first step, 3-amido-2-amino-4,5,6,7-tetrahydro-1-benzothiophene is coupled to methyl thioether as shown under benzaledehdye. Then, the chloro substituted reactant is oxidized by addition of TMAO to reaction medium. The final product can then be isolated chromatography.

Particularly, in the reaction illustrated in FIG. 5B shows the preparation of compounds of the general formula (III) illustrated in FIG. 2.

FIG. 6A, similar to FIGS. 4A and 5A, illustrates a one pot substitution reaction of 2-amino-4,5,6,7-tetrahydro-1-benzothiophene (substituted with groups $R_1$-$R_4$ in the defined positions as illustrated)—at position 3 by amido coupled to piperazine bearing N—$R_5$ group.

FIG. 6B illustrates a coupling reaction between 3-amido 2-amino-4,5,6,7-tetrahydro-1-benzothiophene reactant (substituted with groups $R_1$-$R_5$ in the defined positions as illustrated) and a reactant bearing a $R_7$ group. In this case, the 2-amino group of the substituted 2-amino-4,5,6,7-tetrahydro-1-benzothiophene is coupled with an acyl chloride derivative bearing the $R_7$ group to form an amide bond. The final product can then be isolated chromatography.

Particularly, in the reaction illustrated in FIG. 6B shows the preparation of compounds of the general formula (IV) illustrated in FIG. 2, the 3-amido-2-amino-4,5,6,7-tetrahydro-1-benzothiophene (substituted with groups $R_1$-$R_5$ in the defined positions as illustrated) is dissolved in aqueous NaOH and the acyl chloride derivative is dissolved in ether. The 3-amido-2-amino-4,5,6,7-tetrahydro-1-benzothiophene (substituted with groups $R_1$-$R_5$ in the defined positions as illustrated) is added to a conical flask and the acyl chloride derivative is added dropwise to the aqueous solution overnight at 20° C. The resulting mixture is purified by chromatography to isolate compounds of formula (IV).

Alternatively, the novel RORs modulators of Formula (I), (II), (III), or (IV) represented by the compounds 1 to 23 may be synthetized by combinatorial chemistry.

Combinatorial chemistry has emerged in recent decades as an approach to quickly and efficiently synthesize large numbers of potential small molecule drug Candidates. In a typical synthesis, only a single target molecule is produced at the end of a synthetic scheme, with each step in a synthesis producing only a single product. In a combinatorial synthesis, when using only a single starting material, it is possible to synthesize a large library of molecules using identical reaction conditions that can then be screened for their biological activity. This pool of products is then split into three equal portions containing each of the three products, and then each of the three individual pools is then reacted with another reagent, producing 9 unique compounds from the previous 3. This process is then repeated until the desired number of building blocks is added, generating many compounds.

The use of solid phase supports greatly simplifies the synthesis of large combinatorial libraries of compounds. This is done by anchoring a starting material to a solid support and then running subsequent reactions until a sufficiently large library is built, after which the products are cleaved from the support. The use of solid-phase purification has also been demonstrated for use in solution-phase synthesis schemes in conjunction with standard liquid-liquid extraction purification techniques.

Example 2

Affinities of Compounds 1 to 23

Compounds 1 to 23 were tested on recombinant human RORγT-LBD GST-tagged cells by time-resolved fluorescence energy transfer (TR-FRET) binding assay. This assay measures co-activator peptide RIP140 and RORγT-LBD binding kinetics by quantifying the ability of molecules to inhibit or enhance the activity of RORγ.

Reagents Used to Perform the TR-FRET Binding Assay

| Name | Units/amounts | Source | Catalog Number | Storage |
|---|---|---|---|---|
| Biotin RIP140 peptide | 1 mg | CPC Scientific Inc. | 932851 | −80° C. |
| GST-RORγ (LBD) | 100 μl (0.5 mg/ml) | CreativeBiomart | RORC-114H | −80° C. |
| DMSO | 20 ml | Bioshop | DMS555.1 | RT |
| SureLight Allophycocyanin-Streptavidin | 1 mg | PerkinElmer | CR130-100 | 4° C., in the dark |
| LANCE ® Eu-W1024 labeled anti-GST antibody | 10 μg | PerkinElmer | AD0252 | 4° C. |

Assay Buffer Used to Perform the TR-FRET Binding Assay

| Master Buffer | Storage |
|---|---|
| 50 mM Tris-HCl pH 7.0, 150 mM NaCl, 50 mM KCl, 5 mM $MgCl_2$, pH 7.4 | RT |
| 1M Dithiothreitol (DTT), (1 mM final) | −20° C. |
| 7.5% BSA. (0.1 final) | 4° C. |

Equipment Used to Read the Results of the TR-FRET Binding Assay

| Name | Source | Catalog Number |
|---|---|---|
| OptiPlate-384, White Opaque 384-well Microplate | PerkinElmer | 6007290 |
| Thermo Scientific ™ Nunc ™ 96-Well Polystyrene Conical Bottom MicroWell ™ Plates for compound buffer dilution | Fisher Scientific | 12-565-216 |
| EnSpire multimode plate reader | PerkinElmer | |

Experimental Conditions for Performing the TR-FRET Binding Assay

5 μl of compound in assay buffer plus 15 μl of detection mix for 20 μL total assay volume (50 mM Tris-HCl pH 7.0, 150 mM NaCl, 50 mM KCl, 5 mM MgCl2, 1 mM DTT, 0.1% BSA, 0.001% triton X); 5 nM GST-RORγt (LBD); 90 nM biotinylated RIP140 derived co-activator peptide (biotinyl-NH-Ahx-NSHQKVTLLQLLLGHKNEEN-CONH2); 50 nM SA-APC; 1.5 nM Eu-Anti GST IgG; 1.0% DMSO).

Protocol Followed to Perform the TR-FRET Binding Assay

Compound dilutions (200× in pure DMSO) were prepared by making a 0.5 mM dilution from a 10 mM stock using 100% DMSO. 4.67-fold dilutions of the compounds were then prepared for 11 points beyond the 20 μM starting concentration. For example, 25 μl of 10 mM of the compound was added into 475 μl of DMSO, and 4.07 μl of the resulting solution was titrated into 97.69 μl of DMSO. Subsequently 2 μl of 200× of the test compound in 100% DMSO was diluted into 98 μl of assay buffer in the compound buffer dilution plate to result in a 4× compound solution. 5 μl of the solution is added to 15 μl of assay buffer containing all the assay ingredients to result in a final DMSO concentration of 0.5%.

A 4× solutions containing Europium-labeled antibody, and GST-RORγ (LBD) mixture was prepared, then 5 μl of each solution was added to each well on a 384-well plate, followed by the addition of 5 uL of each concentration of a compound previously diluted in assay buffer (described above). Assay controls (0% inhibition and 100% inhibition controls) were added into columns 1,2, 23, and 24 of the 384 well assay OptiPlate. For the 0% inhibition control, 2 μL of 100% DMSO was added into 98 μl of assay buffer. For the 100% inhibition control, 2 μl of 20 μM GSK2981278 (200×, 100 nM final concentration) was added.

The plate was shaken for one minute, centrifuged at 1000 rpm for 10 seconds, then incubated at 4° C. for overnight and followed by the addition of 5 uL of 4× biotinylated RIP140 peptide & Streptavidin-APC, and read on a plate reader.

For assay screening, Enspire plate reader was used. The settings were as follows: Excitation: 320 nm, Emission A: 615 nm; time delay: 220 μs; window: 600 μs, Emission B: 699 nm (delay time 400 μs, window 800 μs); number of flashes: 100.

In the final assay plate setup, there were sixteen compounds per 384 well plate. The DMSO controls (0% Inhibition) were in columns 23 and 24. The 25 μM T0901317 controls (100% Inhibition) were in columns 1 and 2. The compound titrations were in columns 3-22. Ten-point IC50 curves were generated with n=2 per concentration.

Data Analysis

The RORγT FRET assay is an end point assay with a readout (emission ratio) of acceptor/donor multiplied by 10000. The assay dose response testing is performed in duplicate points per concentration, with ten dilution concentrations per compound curve. The conversion of raw data to % Activity is performed using assay controls, where 100% Activity is represented by the average DMSO controls. Zero percent Activity is the average of two wells of 100 nM, GSK2981278 compound controls/row. IC curve fitting is performed using GraphPad prism, and fitting to the sigmoidal dose-response (variable slope) equation as follows: Y=100/(1+10^((Log IC50−X)*HillSlope) where X is the logarithm of concentration and Y is the normalized response. Y begins at the bottom (0%) and goes to top (100%) with a sigmoid shape. IC50 is the concentration of agonist that gives a response half-way between Bottom and Top. This is not the same as the response at Y=50. Depending on which units Y is expressed in, and the values of Bottom and Top, the IC50 may give a response nowhere near "50". Prism reports both the IC50 and its log.

Results

Compounds 1,2, 3, 4, 5, 6, 7, 8, 9, 10, 11, 12, 13, 14, 15, 16, 17, 18, 19, 20, 21, 22 and 23 were all found to have mean pIC50 values above or equal to 12.

REFERENCE

For a representative example of this assay, see Guendisch, U., Weiss, J., Ecoeur, F., Riker, J. C., Kaupmann, K., Kallen, J., Guntermann, C. (2017). Pharmacological inhibition of RORγt suppresses the Th17 pathway and alleviates arthritis in vivo. PloS one, 12(11), e0188391. doi:10.1371/journal-.pone.0188391.

Example 3

Inhibition of T-Helper 17 Cells Polarization by Compounds 1 to 23

Compounds 1 to 23 were tested for their ability to inhibit Th17 polarization of human peripheral blood mononuclear cells. This assay measures the phenotypic effects of the compounds on the production of interleukin 17A (IL-17A). IL-17A genes are regulated by ROR response elements (ROREs). Compounds that bind to ROR (LBD) can inhibit the binding of RORγ to ROREs DNA site. Compounds can also reduce the effect of the binding which is enhanced by the binding of the co-activator protein.

Reagents Used to Perform the Th17 Polarization Assay

| Name | Units/amounts | Source | Catalog Number | Storage |
|---|---|---|---|---|
| Dynabeads human T-activator CD3/CD28 | 0.4 ml | Life technologies | 111.61D | 4° C. |
| Fetal Bovine Serum (FBS) | 500 ml | Wisent bioproducts | 080450 | −20° C. |
| RPMI 1640 medium, HEPES | 500 ml | Life technologies | 22400089 | 4° C. |
| Penicillin-Streptomycin solution 100X | 100 ml | Wisent bioproducts | 450201EL | −20° C. |
| MEM non-essential amino acids 100X | 100 ml | Wisent bioproducts | 321011EL | −20° C. |
| L-Glutamine 200 mM solution 100X | 100 ml | Wisent bioproducts | 609065EL | −20° C. |
| Sodium pyruvate 100 mM solution 100X | 100 ml | Wisent bioproducts | 600110EL | −20° C. |
| Cell Stimulation Cocktail (500X) | 100 μl | Life technologies | 00497093 | −20° C. |

Reagents Used for Isolating and Storing Peripheral Blood Mononuclear Cells

| Name | Units/amount | Source | Catalog Number | Storage |
|---|---|---|---|---|
| Lymphocyte separation medium | 500 ml | Wisent bioproducts | 305010CL | RT |
| Phosphate buffered saline PBS 10X | 500 ml | Wisent bioproducts | 311012CL | RT |
| DMSO tissue culture grade | 100 ml | Millipore Sigma | D2650 | RT |

-continued

| Name | Units/amount | Source | Catalog Number | Storage |
|---|---|---|---|---|
| Fetal Bovine Serum (FBS) | 500 ml | Wisent bioproducts | 080450 | −20° C. |

Reagents Used for Intracellular Staining

| Name | Units/amount | Source | Catalog Number | Storage |
|---|---|---|---|---|
| Foxp3/ Transcription Factor Staining Buffer Set | Set | Life technologies | 00-5523-00 | 4° C. |

Other Equipment and Materials

| Name | Source | Catalog Number |
|---|---|---|
| Polystyrene tissue culture 96 well plate | Celltreat | 229190 |
| 50 ml centrifuge tubes (sterile) | Progene | 715000B |
| 15 ml Centrifuge Tubes (sterile) | Progene | 711500B |
| 10 ml serological pipettes (sterile) | Progene | 857128 |
| Round-Bottom Polystyrene Tubes | Fisher Scientific | 149595 |
| BD LSRFortessa flowcytometer | BD Biosciences | |

Peripheral Blood Mononuclear Cells Isolation

Peripheral blood mononuclear cells were isolated by density gradient centrifugation. The principle of this method is that components of the blood have different densities and can be separated according to their relative density. Lymphocyte separation medium is a density gradient medium that contains sodium diatrizoate, polysaccharides, and water, and has a density of 1.08 g/ml. This medium is denser than lymphocytes, monocytes, and platelets and they remain about it, but less dense than granulocytes and erythrocytes, which will drop below it. To isolate PBMCs, whole blood was diluted with 1×PBS and then layered gently over 14 ml of separation medium in a 50 ml centrifuge tube and centrifuged for 30-40 minutes at 400×g acceleration 0 and deceleration 0. Four layers were form, each containing different cell types—the uppermost layer contain containing plasma was removed by pipetting. PBMCs layer and is a characteristically white and cloudy "blanket" was gently removed using a 10 ml pipette and added to warm medium or PBS (1:3) to wash off any remaining platelets and centrifuged at 400×g for 10 minutes. The pelleted cells were counted, and the percentage viability estimated using Trypan blue staining. Cells were frozen for long-term storage.

Peripheral Blood Mononuclear Cells Storage

To preserve PBMCs at ultra-low temperatures in liquid nitrogen, dimethyl sulfoxide (DMSO) was used as a cryoprotectant to reduce the formation of ice crystals and prevent cell damage. To freeze, freshly isolated PBMCs are resuspended to $5\times10^6$ cells/mL in freezing medium containing 10% DMSO and 90% fetal bovine serum (FBS) and were placed inside a freezing container at −80° C. overnight to allow gradual and even cooling. The following day, samples were moved to a liquid nitrogen tank for long-term storage.

Culture Media Preparation 10% FBS RPMI Complete Media 500 ml bottle of RPMI at 4° C. was opened in a biological safety cabinet. Half of the media was transferred to a 500 ml 0.22 um bottle top filter (with the vacuum turned off). 59 ml filtered heat inactivated fetal bovine serum (FBS), 6 ml penicillin-streptomycin solution (100×), 6.0 ml of L-glutamine (100×), 6.0 ml MEM non-essential amino acids 100×, 6.0 ml of sodium pyruvate were added and the volume was brought up to 500 ml by adding the RPMI. Culture media were stored in 4° C. and used for duration of two weeks.

Thawing and Resting of PBMCs

PBMCs were thawed carefully to avoid loss of cell viability and functionality. Samples are removed from liquid nitrogen and placed on ice, after which they were thawed in a 37° C. water bath. Once there is a small crystal of ice left in the bottom on the tubes, 500 μL warm complete RPMI medium supplemented with 10% FBS, 1% penicillin-streptomycin, and L-glutamine was added dropwise. The cells were then transferred to Falcon tubes containing 10 mL warm medium and centrifuged for 10 minutes at 400×g to wash off the toxic DMSO. This wash step was repeated, and the cell pellet was then resuspended in medium to count as before. Once thawed, PBMCs was rested overnight to remove any apoptotic cell this increases viability and improves functionality and involves incubating the freshly thawed PBMCs in supplemented medium for approximately 18 hours. After this resting period, cells were washed to be used in culture.

Th17 Polarization Protocol

PBMCs were plated in 96 well plates using complete RPMI-1640 medium (10% FBS), and incubated at 37° C. in a humidified, 5% $CO_2$ atmosphere. Cells were treated with CD3/CD28 (2 μl: 80000 cells) for 12 days in presence of IL-6 10 ng/ml, IL-1B 10 ng/ml, TGF-B 10 ng/ml, and IL-23 10 ng/ml. Culture medium was changed every other day for the whole duration. Compounds were added to the polarized cells at day 12 for 48 hours. At measurement day, CD3/CD28 beads were removed and cells were treated with cell stimulation cocktail for 5 hours at the end of 48 hours incubation. Plates were centrifuged at 400×g for 10 minutes. Supernatant was collected for further testing and cells were resuspended in 1×PBS and washed twice at 400×g before staining for surface and intracellular markers.

Intracellular Cytokines Staining

PBMCs cell suspension were stained cells with Live/dead (455 UV) viability dye. The dye was used in 1:1000 concentration in 1×PBS. The cells were incubated in dye solution for 30 minutes in 4° C. Control wells were used where 50% of the cells in those wells were killed by heat (65° C. for 1 minute) and then returned to their respective wells and stained similarly for 30 minutes. Cells were then centrifuged at 400×g for 10 minutes and the dye solution was discarded. Cells were washed twice with 1×PBS before surface staining. After the last wash, supernatant was discarded, and plates were pulse vortexed to completely dissociate the pellets. Anti-human antibodies for cell surface antigens namely CD4, CD3 and CD8 were added to each well at 1:1000 concentration in 1% BSA in PBS. Cells were incubated for 1 hour in 4° C. Cells were then centrifuged at 400×g and washed with 1×PBS twice. After the last wash, supernatant was discarded, and plates were pulse vortexed to completely dissociate the pellets. Cells were then treated with FOXP3 fixation/permeabilization buffer (100 μl/well) for 30 minutes at 4° C. Plates were centrifuged at 400×g and buffer was discarded followed by two washing steps with FOXP3 permeabilization buffer (200 μl) and centrifugation at 400×g. Anti-human antibodies for IL17A, RORγt, IL21, IL22 and IFNγ were added to each well used at 1:1000 concentration in permeabilization buffer. Cells were incubated for 1 hour in 4° C. Cells were then centrifuged at 400×g and washed with 1×PBS twice. Cell quantification, viability and Intracellular cytokines expression was analyzed by flowcytometry using BD LSRFortessa flow cytometer.

Degree of Th17 polarization was measured by the percentage of IL17A positive cells relative to the total CD4 T cells. Inhibition of Th17 polarization is defined as significant reduction in the percentage of IL17A positive cells. Each test compound was tested at 10 nM concentration in triplicates against 8 replicates of control wells. The data were analyzed using one-way ANOVA and Bonferroni.

Results

Compounds 1, 2, 3, 4, 5, 6, 7, 8, 9, 10, 11, 12, 13, 14, 15, 16, 19, 20, 22, and 23 inhibited the polarization of Th17 cells by average of 50% (30-70%), $p<0.05$.

REFERENCE

For representative examples of this assay, see Gaffen S L. An overview of IL-17 function and signaling. Cytokine. 2008; 43:402-407; Bettelli E, Korn T, Oukka M, Kuchroo V K. Induction and effector functions of T(H)17 cells. Nature. 2008; 453:1051-1057; Veldhoen M, Hirota K, Christensen J, O'Garra A, Stockinger B. Natural agonists for aryl hydrocarbon receptor in culture medium are essential for optimal differentiation of Th17 cells. J Exp Med. 2009; 206:43-49; and Laurence A, Tato C M, Davidson T S, et al. Interleukin-2 signaling via STAT5 constrains T helper 17 cell generation. Immunity. 2007; 26:371-381.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A pharmaceutical compound selected from the group consisting of:

N-(3-(4-benzylpiperazine-1-carbonyl)-4,5,6,7-tetrahydro-benzo[b]thiophen-2-yl)-2-fluorobenzamide;

N-(3-(benzylcarbamoyl)-4,5,6,7-tetrahydrobenzo[b]thiophen-2-yl)-5-chloro-2-(methylthio)pyrimidine-4-carboxamide;

N-(6-ethyl-3-{[(2-methylphenyl)amino]carbonyl-4,5,6,7-tetrahydro-1-benzothien-2-yl)-1-methyl-1H-pyrazole-5-carboxamide;

N-{6-tert-butyl-3-[(4-methyl-1-piperazinyl)carbonyl]-4,5,6,7-tetrahydro-1-benzothien-2-yl}-2-fluorobenzamide;

2-fluoro-N-{6-methyl-3-[(4-methyl-1-piperazinyl)carbonyl]-4,5,6,7-tetrahydro-1-benzothien-2-yl}benzamide;

N-benzyl-2-[(trifluoroacetyl) amino]-4,5,6,7-tetrahydro-1-benzothiophene-3-carboxamide;

N-benzyl-2-({[(4-methyl-2-pyrimidinyl)thio] acetyl}amino)-4,5,6,7-tetrahydro-1-benzothiophene-3-carboxamide;

N-benzyl-2-[(1-piperidinylacetyl) amino]-4,5,6,7-tetrahydro-1-benzothiophene-3-carboxamide;

N-benzyl-2-{[(4-methyl-1-piperazinyl) acetyl]amino}-4,5,6,7-tetrahydro-1-benzothiophene-3-carboxamide;

N-benzyl-2-{[(4-methyl-1-piperidinyl) acetyl]amino}-4,5,6,7-tetrahydro-1-benzothiophene-3-carboxamide;

N-(3-(2-methylpyrrolidine-1-carbonyl)-4,5,6,7-tetrahydro-benzo[b]thiophen-2-yl)nicotinamide;

N-(3-((2R,4R)-2,4-dimethylpiperidine-1-carbonyl)-4,5,6,7-tetrahydrobenzo[b]thiophen-2-yl)nicotinamide;

N-(3-(((1r,4r)-4-hydroxycyclohexyl)carbamoyl)-4,5,6,7-tetrahydrobenzo[b]thiophen-2-yl)nicotinamide;

N-(3-(3-ethylpyrrolidine-1-carbonyl)-4,5,6,7-tetrahydro-benzo[b]thiophen-2-yl)nicotinamide;

N-benzyl-2-(2-((1-methyl-1H-imidazol-2-yl)thio)acetamido)-4,5,6,7-tetrahydrobenzo[b]thiophene-3-carboxamide;

N-(3-(3-(hydroxymethyl) pyrrolidine-1-carbonyl)-4,5,6,7-tetrahydrobenzo[b]thiophen-2-yl)nicotinamide;

N-(6,6-dimethyl-3-(morpholine-4-carbonyl)-4,5,6,7-tetrahydrobenzo[b]thiophen-2-yl) pyrazine-2-carboxamide;

N-(3-(((1-methyl-1H-1,2,4-triazol-3-yl)methyl) carbamoyl)-4,5,6,7-tetrahydrobenzo[b]thiophen-2-yl)nicotinamide;

(S)-N-(3-((1-cyanoethyl) carbamoyl)-4,5,6,7-tetrahydro-benzo[b]thiophen-2-yl)nicotinamide; and N-(3-((piperidin-4-ylmethyl) carbamoyl)-4,5,6,7-tetra-hydro-benzo[b]thiophen-2-yl)nicotinamide.

2. A pharmaceutical composition for inhibiting the activity of RORc and RORγt comprising at least one pharmaceutical compound according to claim 1, its acceptable salt thereof, or its stereoisomer thereof; and a pharmaceutically acceptable carrier.

3. A pharmaceutical composition according to claim 2, further comprising one or more additional compounds selected from the group consisting of:

(a) a cytotoxic agent selected from the group consisting of taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, analogs or homologs thereof, or a combination thereof;

(b) an antimetabolite;

(c) an alkylating agent;

(d) an anthracycline;

(e) an antibiotic;

(f) an anti-mitotic agent;

(g) a hormone therapy;

(h) a signal transduction inhibitor;

(i) a gene expression modulator;

(j) an apoptosis inducer;

(k) an angiogenesis inhibitor; and (I) an immunotherapy agent.

4. The pharmaceutical composition of claim 3, wherein said antimetabolite is methotrexate, 6-mercaptopurine, 6-thioguanine, cytarabine, 5-fluorouracil decarbazine, or a combination thereof.

5. The pharmaceutical composition of claim 3, wherein said alkylating agent is mechlorethamine, thiotepa chlorambucil, melphalan, carmustine (BSNU), lomustine (CCNU), cyclothosphamide, busulfan, dibromomannitol, streptozotocin, mitomycin C, cisdichlorodiamine platinum (II) (DDP) cisplatin, or a combination thereof.

6. The pharmaceutical composition of claim 3, wherein said anthracycline is daunorubicin, doxorubicin, or a combination thereof.

7. The pharmaceutical composition of claim 3, wherein said antibiotic is dactinomycin, bleomycin, mithramycin, anthramycin (AMC), or a combination thereof.

8. The pharmaceutical composition of claim 3, wherein said anti-mitotic agent is vincristine, vinblastine, or a combination thereof.

9. The pharmaceutical composition of claim 3, wherein said signal transduction inhibitor is imatinib, trastuzumab, or a combination thereof.

10. The pharmaceutical composition of claim 3, wherein said gene expression modulator is a siRNA, a shRNA, an antisense oligonucleotide, an HDAC inhibitor, or a combination thereof.

11. The pharmaceutical composition of claim 3, wherein said immunotherapy agent is a monoclonal antibody, a chimeric antigen receptors (CARs) T-Cell, or a combination thereof.

12. The pharmaceutical composition of claim 3, wherein said hormone therapy is a luteinizing hormone-releasing hormone (LHRH) antagonist.

13. The pharmaceutical composition of claim 3, wherein said apoptosis inducer is a recombinant human TNF-related apoptosis-inducing ligand (TRAIL).

14. The pharmaceutical composition of claim 3, wherein said angiogenesis inhibitor is sorafenib, sunitinib, pazopanib, everolimus or a combination thereof.

* * * * *